(12) United States Patent
Salamone et al.

(10) Patent No.: US 8,829,053 B2
(45) Date of Patent: Sep. 9, 2014

(54) BIOCIDAL COMPOSITIONS AND METHODS OF USING THE SAME

(75) Inventors: Joseph Salamone, San Antonio, TX (US); Ann Beal Salamone, San Antonio, TX (US)

(73) Assignee: Rochal Industries LLP, San Antonio, TX (US)

( * ) Notice: Subject to any disclaimer, the term of this patent is extended or adjusted under 35 U.S.C. 154(b) by 0 days.

(21) Appl. No.: 13/313,880

(22) Filed: Dec. 7, 2011

(65) Prior Publication Data
US 2013/0150451 A1 Jun. 13, 2013

(51) Int. Cl.
A61K 31/155 (2006.01)
A61K 31/14 (2006.01)
A61K 31/08 (2006.01)
A61K 31/045 (2006.01)

(52) U.S. Cl.
USPC ........... 514/635; 514/642; 514/722; 514/724; 514/738

(58) Field of Classification Search
USPC ................................. 514/635, 642, 722, 724
See application file for complete search history.

(56) References Cited

U.S. PATENT DOCUMENTS

| | | | |
|---|---|---|---|
| 3,428,576 A | 2/1969 | Dickinson et al. | |
| 4,670,592 A | 6/1987 | Eakin et al. | |
| 4,758,595 A | 7/1988 | Ogunbiyi et al. | |
| 5,516,510 A | 5/1996 | Beilfuss et al. | |
| 5,858,937 A | 1/1999 | Richard et al. | |
| 5,990,174 A | 11/1999 | Henry | |
| 6,106,854 A | 8/2000 | Belfer et al. | |
| 6,143,244 A | 11/2000 | Xia et al. | |
| 6,846,846 B2 | 1/2005 | Modak et al. | |
| 7,670,997 B2 | 3/2010 | Burke et al. | |
| 8,281,445 B2 * | 10/2012 | Adkins et al. | 15/104.93 |
| 2004/0059006 A1 | 3/2004 | Beilfuss et al. | |
| 2004/0082925 A1 * | 4/2004 | Patel | 604/289 |
| 2004/0219227 A1 * | 11/2004 | Modak et al. | 424/641 |
| 2005/0084471 A1 * | 4/2005 | Andrews et al. | 424/70.31 |
| 2006/0051385 A1 | 3/2006 | Scholz | |
| 2007/0148099 A1 | 6/2007 | Burke et al. | |
| 2007/0202006 A1 | 8/2007 | Ammon et al. | |
| 2007/0237812 A1 * | 10/2007 | Patel et al. | 424/446 |
| 2007/0282008 A1 | 12/2007 | Mason | |
| 2007/0286767 A1 | 12/2007 | Burke et al. | |
| 2007/0287752 A1 | 12/2007 | Burke et al. | |
| 2008/0131470 A1 * | 6/2008 | Witham et al. | 424/402 |
| 2009/0035335 A1 * | 2/2009 | Marotta et al. | 424/401 |
| 2009/0170947 A1 * | 7/2009 | Aggarwal et al. | 514/566 |
| 2009/0202615 A1 | 8/2009 | Rodeheaver et al. | |
| 2009/0300864 A1 * | 12/2009 | Adkins et al. | 15/104.93 |
| 2010/0305211 A1 | 12/2010 | Modak et al. | |
| 2011/0189260 A1 | 8/2011 | Herr et al. | |

FOREIGN PATENT DOCUMENTS

| | | | | |
|---|---|---|---|---|
| WO | WO2008/154395 | * | 12/2008 | A01N 25/00 |
| WO | WO 2008154395 A1 | * | 12/2008 | A01N 25/00 |

OTHER PUBLICATIONS

Schneider, L. A., et al. Influence of pH on wound-healing: a new perspective for wound-therapy. Arch. Dermatol. Res. (2007) vol. 298 pp. 413-420.*
Kubo, I., et al. Structural Functions of Antimicrobial Long Chain Alcohols and Phenols. Bioorganic and Medicinal Chemistry. vol. 3, pp. 873-880. Published 1995.*
Shelef et al. Food Science and Technology vol. 145, pp. 573-598. Published 2005.*
Monk et al. J. of Applied Bacteriology vol. 81, pp. 7-18. Published 1996.*
Schneider et al. Arch. Dermatol. Res. vol. 298, pp. 413-420. Published 2007.*
Monk, J.D., et al. Journal of Applied Bacteriology vol. 81, pp. 7-18. Published 1996.*
Yanai, R., et al., Eye and Contact Lens vol. 37 pp. 85-89, published Mar. 2011.*
James, Garth A., et al., Biofilms in Chronic Wounds, Wound Rep Reg (2008) 16 pp. 37-44.
B. Braun, Protosan and Askina, Clinical and Scientific Evidence, B. Braun Hospicare Ltd, Ireland and B. Braun Medical AG, Switzerland, Jun. 1, 2012.
Harbs, et al., In Vitro Efficacy of Octenidine and Polihexanide Against Biofilms Composed of *Pseudomonas aeruginosa*, Journal, GMS Krankenhaushyg Interdiszip 2007; 2(2):Doc45, published; Dec. 28, 2007.
Activa Healthcare, PHMB, found at http://www.activahealthcare.co.uk/casestudies-files/PHMB_Quick_Fact_Card.pdf, Jan. 2012.

* cited by examiner

*Primary Examiner* — Paul Zarek
*Assistant Examiner* — George W Kosturko
(74) *Attorney, Agent, or Firm* — Duane Morris LLP; J. Rodman Steele, Jr.; Gregory M. Lefkowitz

(57) ABSTRACT

An antimicrobial composition with synergistic biocidal activity is described which comprises at least one antimicrobial polymeric biguanide and at least one antimicrobial vicinal diol, said vicinal diol comprises at least one monoalkyl glycol, monoalkyl glycerol, or monoacyl glycerol, to diminish or eliminate biofilm communities. Such synergistic interaction is effective in wound treatment, particularly for chronic wounds, burns and battlefield-induced wounds, as well as for disinfecting non-biological surfaces. The antimicrobial composition can also be prepared as viscous solutions or as gels. The antimicrobial composition may be added to a substrate and dried, such as to a catheter, or to a foam, or to a fiber wound dressing, or coated as a viscous solution or gel upon such devices, to provide controlled release antimicrobial activity.

49 Claims, 3 Drawing Sheets

BIOCIDAL COMPOSITIONS AND METHODS OF USING THE SAME

FIELD OF THE INVENTION

This invention relates generally to the formation of an antimicrobial composition that is highly effective against microbial infestation of acute and chronic wounds. The antimicrobial gel is related to the water-based solution in composition, but has a higher viscosity because of added viscosity enhancing or gelling agents.

BACKGROUND OF THE INVENTION

The primary function of non-compromised, intact skin is to control the various microbes that reside on the skin surface, thus preventing underlying tissue from being colonized by potentially pathogenic species. When a wound occurs, subcutaneous tissue is exposed, leading to a moist, nutritious environment for microbial colonization and proliferation. Wound colonization is often polymicrobial, involving organisms that are potentially pathogenic. If infection occurs, particularly for chronic wounds, the wound may fail to heal. The consequences of this occurrence are traumatic for the patient, with greatly increased medical expenses.

Chronic wounds include pressure ulcers, diabetic foot ulcers, and venous leg ulcers. These wounds are difficult to heal and contribute to persistent individual health problems as well as markedly increasing health care costs. It is believed that bacteria colonizing chronic wounds exist as highly persistent biofilm communities (G. A. James, et al., Wound Repair Regen., 16(1), 37-44, 2008). Biofilm formation appears to be an important contributing factor in delayed wound healing.

It does not appear that the bacteria present on the surface of chronic wounds are present as planktonic cells or even simple primary attachment modes. Rather, such colonization is believed to be by biofilm formation, often of mixed microbial species within a matrix of extracellular hydrophilic polysaccharides. Bacteria living in a biofilm have significantly different properties from planktonic bacteria, as the protected environment of the polymer coating allows them to cooperate and interact. A biofilm has the ability to neutralize host defenses and commandeer host systems, and possesses a vast array of defenses and virulence factors. One feature of this environment is increased resistance to detergents and antibiotics, as the dense extracellular matrix and the outer layer of cells protect the interior of the community.

While biofilms are commonly present on chronic wounds, they are less prominent on acute wounds. Clinically, there is a significant difference in the healing behavior between chronic wounds and acute wounds, with the latter being more facile. Suppression of the biofilm bioburden using multiple simultaneous strategies including debridement, anti-biofilm agents, specific biocides, antibiotics and advanced technologies does enhance wound healing.

Wounds are an ideal environment for the formation of biofilm communities because of their susceptibility to contamination and the availability of substrate and nutrients for biofilm attachment. Chronic wound infections share two important attributes with other biofilm diseases: persistent infection that is not cleared by the host immune system, and resistance to systemic and topical antimicrobial agents. In the absence of a biocidal wound cleanser solution, frequent debridement is often a clinically effective treatment to help heal chronic wounds.

Biofilms reportedly cause an estimated 1 million nosocomial infections each year in the United States. Both aerobic and anaerobic bacteria have been found. Some studies have isolated the most common microorganism (*Staphylococcus epidermidis*) that triggers biofilm infections, while many other organisms have been isolated. Common bacteria found in biofilms include Gram positive *Enterococcus faecalis, Staphylococcus aureus, Micrococcus* spp. and beta-hemolytic *Streptococcus* (*S. pyogenes, S. agalactiae*) as well as Gram-negative bacteria of *Escherichia coli, Klebsiella pneumoniae, Proteus mirabilis, Pseudomonas aeruginosa, Acinetobacter baumannii* and *Stenotrophomonas maltophilia*.

In addition to biofilms in chronic wounds, biofilms are involved in approximately 90% of all chronic human infections and 65% of all hospital-acquired infections. Biofilms are responsible for otitis media, the most common acute ear infection. Biofilms are also involved in bacterial endocarditis, an infection of the inner surface of the heart and its valves. Biofilms are also found in patients with cystic fibrosis, a chronic disorder resulting in increased susceptibility to serious lung infections. Additionally, biofilms are also reported to be involved with Legionnaire's disease, an acute respiratory infection resulting in *Legionnella* biofilms, a ubiquitous aquatic organism that can be present in air and water heating/cooling and distribution systems. Biofilms are also involved with periodontal disease, dental plaque, transplant infections, infections of indwelling medical devices (e.g., catheter, prostheses), contaminated clinical surfaces and reusable instruments.

For healing of acute and chronic wounds colonized by microorganisms, proper cleaning is essential. Most commercial wound cleansers are based predominantly upon surfactant cleaning and are designed to soften and remove necrotic tissue and debris. These aqueous solutions have used a surfactant with or without a preservative, with or without a buffer, and with or without a chelating agent.

U.S. Patent Publication No. 2004/0059006 describes a disinfectant composition comprising 1-(2-ethylhexyl)glycerol ether (octoxyglycerin, Sensiva® SC 50) and one or more aromatic alcohols, such as aryloxyalkanols, oligoalkanol aryl ethers or arylalkanols. The composition is said to be useful for controlling mycobacteria. No studies were performed on *Mycobacterium* biofilms.

U.S. Pat. No. 6,106,854 discusses a liquid that has germicidal and biofilm cleansing properties, comprising an anti-infective, an antiseptic agent, and an anti-biofilm agent, a water purifying agent, a sanitizer and a bactericide, wherein the bactericide includes chlorhexidine, in a concentration of 10.0% to 23.0% of the disinfectant concentration.

U.S. Pat. No. 6,143,244 discusses compositions for cleaning and disinfecting contact lenses wherein a polymeric biguanide is used in combination with bis(biguanides) as disinfectants, which will reduce microbial bioburden by two log orders in four hours and preferably by one log order in one hour. The examples utilize 0.8 ppm (0.00008 wt %) poly (hexamethylene biguanide) and 2 ppm (0.0002 wt %) of alexidine. This low concentration of biguanide is used in a regimen procedure according to FDA Chemical Disinfection Efficacy Test—July, 1985, Contact Lens Solution Draft Guidelines, utilizing bacteria in colony forming units and does not evaluate the efficacy against bacterial biofilms.

U.S. Pat. No. 6,846,846 and U.S. Patent Application Number 2010/0305211 discuss a combination of a biguanide and a branched monoalkyl alcohol, namely octoxyglycerin, (Sensiva® SC 50, glycerol 1-(2-ethylhexyl ether), or 1-(2-ethylhexyl)glycerin), for use as a gentle-acting skin disinfectant. Additional ingredients, particularly quaternary ammonium compounds, and particularly benzalkonium chloride, are shown to be effective against bacteria in colony forming units. This patent and application do not discuss the use of a biguanide and a branched monoalkyl glycol in eliminating a bacterial biofilm.

Octoxyglycerin is sold under the trade name Sensiva® SC 50 (Schülke & Mayr). It is a branched, glycerol monoalkyl ether known to be gentle to the skin and to exhibit antimicrobial activity against a variety of Gram-positive bacteria, such as *Micrococcus luteus, Corynebacterium aquaticum, Corynebacterium flavescens, Corynebacterium callunae,* and *Corynebacterium nephredi.* Sensiva® SC 50 is used in various skin deodorant preparations at concentrations between about 0.2 (2,000 ppm) and 3 weight (wt) % (30,000 ppm).

In U.S. Patent Application Number 2007/0287752, an aqueous ophthalmic composition comprising a branched glycerol monoalkyl ether, such as Sensiva® SC 50, present in a total amount of from 0.05 ppm (0.000005 wt %) to 1,000 ppm (0.1 wt %), and an antimicrobial agent, including poly (hexamethylene biguanide) and alexidine, at a concentration of from 0.01 ppm (0.000001 wt %) to 100 ppm (0.01 wt %), with a preference at 3 ppm (0.0003 wt %), where the presence of the branched glycerol compound enhances the biocidal efficacy of the aqueous ophthalmic composition. The compositions are used as a disinfecting solution, a preservative solution or packaging solution for contact lenses. No biocidal studies were conducted on biofilm.

U.S. Pat. No. 7,670,997 discusses an aqueous ophthalmic composition and method of inhibiting the formation of foam in an aqueous ophthalmic composition that includes a surfactant, comprising a branched, glycerol monoalkyl compound and a fatty acid monoester with an antimicrobial agent such as alexidine, chlorhexidine or poly(hexamethylene biguanide). The fatty acid monoester comprises an aliphatic fatty acid portion having six to fourteen carbon atoms and an aliphatic hydroxyl portion, with decanoylglycerol being preferred. In a lens care solution, poly(hexamethylene biguanide) is used in concentration of from 0.01 ppm (0.000001 wt %) to 3 ppm (0.0003 wt %) with alexidine at a concentration of 4.5 ppm (0.00045 wt %), including Sensiva® SC 50 at a concentration of 0.15 wt % (1,500 ppm) and decanoylglycerol at a concentration of 0.12 wt % (1,200 ppm). Synergistic biocidal activity towards colony forming units of *Candida albicans* and *Fusarium solani* is reported for interactions of the branched, glycerol monoalkyl compound and the fatty acid glyceryl monoester. No studies were conducted on biofilm with these ingredients.

U.S. Patent Application Publication 2006/0051385 discusses a method of killing or inactivating microorganisms on mammalian tissue by an antiseptic, a hydrophilic component, a surfactant, and a hydrophobic vehicle, where the antiseptic includes biguanides and bisbiguanides. This study did not include an analysis of biofilm elimination.

U.S. Patent Application Publication 2007/0282008 A1 discusses a polymeric biguanide or a bis(biguanide) compound, a chelating agent and a buffering agent for the prevention or treatment of skin and ear tissue infections. The antiseptic behavior of bis(biguanides), such as alexidine and chlorhexidine, and polymeric biguanides, such as poly(hexamethylene biguanide) (PHMB), is discussed for treatment of infection. However, there is no discussion about the incorporation of a monoalkyl glycol, a monoacyl glycerol, or a glycerol alkyl ether, or the interaction of these individual or combined ingredients with a biofilm.

U.S. Patent Application Publication 2009/0202615 discusses compositions containing high concentrations of a surface active agent (surfactant) and a sub-lethal amount of an antimicrobial agent for contacting a microbial biofilm. The Examples utilize high surfactant concentrations (>45%). The sub-lethal amount of antimicrobial agent is defined as less than the standard therapeutically effective amount to effectively eradicate or inhibit the growth of biofilm forming microorganisms or pathogens, or inhibit biofilm formation or eradicate formed biofilms. This application recommends a sub-lethal amount of the antimicrobial agent, such as silver sulfadiazine, to be equal to or less than 1% by weight (10,000 ppm) of the composition. Regrowth of the biofilm was not considered.

U.S. Patent Application 2007/0202006 discusses the use of one or more biguanides to kill bacterial endospores, particularly from the genus *Bacillus* and the genus *Clostridium*. This study did not include the use of an antimicrobial vicinal diol. Additionally, biofilm elimination was not considered.

U.S. Pat. No. 5,516,510 discusses deodorant compositions containing poly(hexamethylene biguanide) at a concentration of from 0.01% to 0.5% with a short chain monohydric alcohol, such as ethanol at a concentration of 20-80%, in a nonpolar propellant, which also contains water and a polarity modifier, the latter including dodecanol, 1-(2-ethylhexyl) glycerol ether (Sensiva® SC 50), and ketones such as acetone. The amount of monohydric short chain alcohol and nonpolar propellant can be as high as 99%. There is no discussion on the elimination of a short chain monohydric alcohol or a polarity modifier such as acetone, both of which can cause irritation and stinging on skin, or the use of such a composition to reduce or eradicate biofilm.

The use of commercial wound cleansers that incorporate a biocidal agent have recently gained in importance, particularly to treat wounds highly infected by microorganisms. Three such commercial products include Prontosan® Wound Irrigation Solution and Gel from Braun Medical, Inc., and Microsyn® Skin and Wound Cleanser and Dermacyn® Wound Care from Oculus Innovative Sciences. Prontosan® Wound Irrigation System is based upon a surfactant with the biocide of poly(hexamethylene bisbiguanide) (PHMB). Prontosan® Wound Irrigation Solution and Gel is used for cleansing, moisturizing and decontaminating acute and chronic wounds to aid in efficient wound bed preparation. The Microsyn® and Dermacyn® Wound Care Solution are active oxychlorine compounds and super-oxidized solutions intended for use in the treatment of infection in acute and chronic wounds and in the debridement, irrigation and moistening of acute and chronic wounds, ulcers, cuts, abrasions and burns. Such products are reported to reduce the microbial load and assist in creating a moist environment in order for the body to perform its own healing process. The biocidel activity of such products appears to be based upon a dilute sodium hypochlorite/hydrochlorous acid solution.

While both Prontosan™ and Microsyn® solutions are reported to reduce the biofilm bioburden of wounds, neither has been reported to eliminate regrowth of the biofilm by providing total kill. It is the intent of this invention to provide a solution that is capable achieving this result in order to provide more rapid, more effective wound healing than exists by current methods.

SUMMARY OF THE INVENTION

The present invention provides an antimicrobial composition that is capable of either reducing a microbial biofilm by 4 log orders in 10 minutes and by elimination of the biofilm with no regrowth within 24 hours. The microbial biofilm eliminated or reduced by 4 log orders can be of a microbe including, but not limited to, *Aspergillus niger, Candida albicans, Staphylococcus aureus, Pseudomonas aeruginosa, Escherichia coli, Enterococci*. Such an antimicrobial solution is particularly effective against biofilms that occur in chronic wounds. It is postulated that the decreased or eliminated biofilm in and on such wounds would greatly expedite wound healing, thus reducing patient suffering and associated medical costs.

An antimicrobial composition exhibiting a synergistic interaction of at least one polymeric biguanide and at least one antimicrobial vicinal diol, where the vicinal diol comprises at least one monoalkyl glycol, monoalkyl glycerol, or monoacyl glycerol, is described. Monoalkyl glycerols are also referred to as glycerol alkyl ethers, while monoacyl glycerols are also referred to as glycerol alkyl esters. The substituents on the monoalkyl glycol, the monoalkyl glycerol and the monoacyl glycerol are preferentially aliphatic, and can be linear or branched, and saturated or unsaturated.

Biguanides have a broad spectrum of activity against bacteria, fungi, protozoa, and viruses, while glycerol alkyl ethers, monoalkyl glycols, and monoacyl glycerols are particularly effective against Gram positive bacteria and yeasts. Surprisingly, the antimicrobial compositions described herein are capable of diminishing or eliminating biofilm formation, particularly in wounds and burns, by complete kill with no regrowth of the microorganism. The antimicrobial composition can be utilized both as a wound irrigation solution and as an antimicrobial wound gel for wound bed preparation. The antimicrobial composition can also be in the form of an aqueous solution or gel that can be used as a surface disinfectant, as a coating on a catheter or on a foam or on other backing and placed upon a wound in either the hydrated form or dried thereon. Additionally, the antimicrobial composition can be used for disposable, absorbent materials, such as on diapers and products for adult incontinence and feminine hygiene, as well as for personal, body wipes, in addition to industrial wipes.

It has unexpectedly been discovered that a synergistic interaction for biofilm reduction and complete elimination can be obtained in an antimicrobial composition comprising at least one polymeric biguanide and at least one antimicrobial vicinal diol. The vicinal diol can include at least one monoalkyl glycol, monoalkyl glycerol, or monoacyl glycerol. The monoalkyl glycol can include an antimicrobial monoalkyl-substituted 1,2-diol; the monoalkyl glycerol can include an antimicrobial glycerol ether, and the monoacyl glycerol can include an antimicrobial glycerol ester.

The antimicrobial compositions described herein can also provide a synergistic interaction between a gel comprising at least one polymeric biguanide and at least one antimicrobial vicinal diol, where the vicinal diol comprises at least one monoalkyl glycol, monoalkyl glycerol, or monoacyl glycerol, to give no re-growth of a microbial biofilm.

The antimicrobial compositions described herein can also provide a synergistic interaction between at least one biguanide and at least one antimicrobial vicinal diol, and a chelating agent to give enhanced reduction or total elimination of a microbial biofilm.

The antimicrobial compositions described herein can also provide a synergistic interaction between at least one biguanide and at least one antimicrobial vicinal diol, as well as, a surfactant and a chelating agent to remove necrotic debris and to give enhanced reduction or total elimination of a microbial biofilm.

The antimicrobial compositions described herein can also include polymeric biguanide—and low molecular weight bis (biguanide)—in combination with other ingredients to synergistically reduce or eliminate microbial biofilm in wounds.

The antimicrobial compositions described herein are also intended to be used to treat acute and chronic wounds, as well as, burn wounds.

The antimicrobial compositions described herein can be used to reduce and eliminate Gram positive and Gram negative bacteria in wounds, surfaces and devices.

The antimicrobial compositions described herein can be used to reduce and eliminate fungi in wounds, surfaces and devices.

The antimicrobial compositions described herein can be used to reduce and eliminate yeast in wounds, surfaces and devices.

The antimicrobial compositions described herein can be used to reduce and eliminate mold in wounds, surfaces and devices.

The antimicrobial compositions described herein can be used to reduce and eliminate protozoa in wounds, surfaces and devices.

The antimicrobial compositions described herein can be used to reduce and eliminate mycoplasma in wounds, surfaces and devices.

The antimicrobial compositions described herein can be used to reduce and eliminate viruses in wounds, surfaces and devices.

The antimicrobial compositions described herein can be used to reduce bacterial growth by incorporation of a chelating agent to the antimicrobial composition.

The antimicrobial compositions described herein can be used to facilitate wound healing by deactivating matrix metalloproteases in a wound by a chelating agent.

The antimicrobial compositions described herein can provide biguanide-containing compositions that are non-cytotoxic to human epidermal and dermal cells.

The antimicrobial compositions described herein can provide biguanide-containing compositions that do not cause tissue irritation upon contact with tissue.

The antimicrobial compositions described herein can provide biguanide-containing compositions that have a pH that is mildly acidic to enhance wound healing.

The antimicrobial compositions described herein can provide biguanide-containing compositions that are mildly hypotonic to enhance biocidal efficacy.

The antimicrobial compositions described herein can incorporate antimicrobial essential oils to augment the antimicrobial activity of the compositions.

The antimicrobial compositions described herein can incorporate antimicrobial essential oils that provide a pleasing fragrance to the compositions.

The antimicrobial compositions described herein can provide a rapid, synergistic biocidal activity against a microbial biofilm.

The antimicrobial compositions described herein can provide a synergistic interaction between one polymeric biguanide and at least one monoalkyl glycol, glycerol alkyl ether, and monoacyl glycerol deposited on a surface or a device to give enhanced or total elimination of a microbial biofilm.

These and other objectives and advantages of the antimicrobial compositions described herein, some of which are specifically described and others that are not, will become apparent from the detailed description and claims that follow.

DETAILED DESCRIPTION OF THE INVENTION

Figure 1:
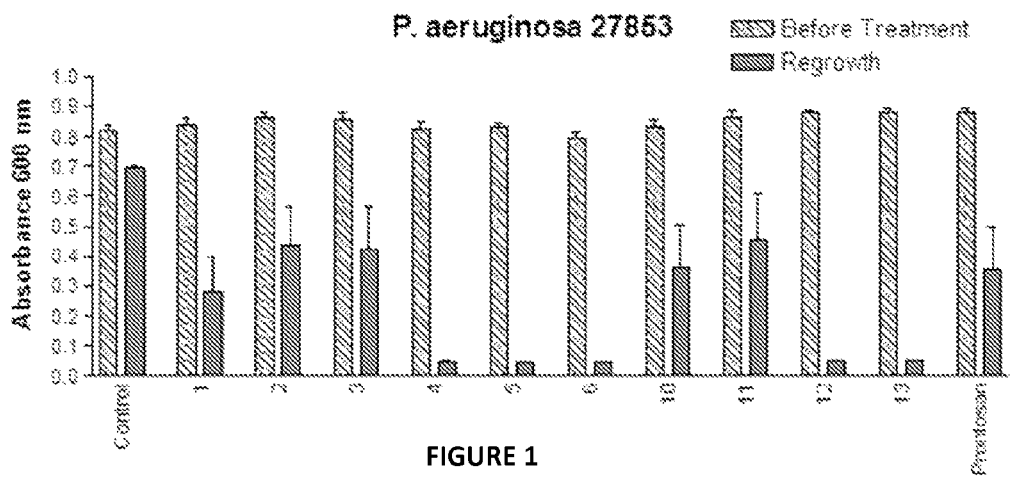
FIG. 1 is a graph showing *Pseudomonas aeruginosa* biofilm regrowth for saline, PRONTOSAN® and solutions 1-6 and 10-13.

Antimicrobial solutions comprising an aqueous mixture of at least one antimicrobial polymeric biguanide and at least one antimicrobial vicinal diol are described. The vicinal diol can include at least one monoalkyl glycol, monoalkyl glycerol, or monoacyl glycerol.

The monoalkyl glycol can have a structure represented as follows:

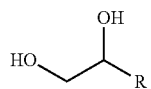

wherein R=$C_3$-$C_{18}$ branched or unbranched alkyl group or alkylene group. In some antimicrobial compositions, R=$C_3$-$C_{12}$ branched or unbranched alkyl group or alkylene group, or R=$C_3$-$C_8$ branched or unbranched alkyl group or alkylene group, or R=$C_3$-$C_8$ branched or unbranched alkyl group.

The monoalkyl glycerol (alternately referenced as a glycerol alkyl ether) can have a structure represented as follows:

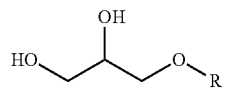

wherein R=$C_3$-$C_{18}$ branched or unbranched alkyl group or alkylene group. In some antimicrobial compositions, R=$C_6$-$C_{15}$ branched or unbranched alkyl group or alkylene group, or R=$C_7$-$C_{12}$ branched or unbranched alkyl group or alkylene group, or R=$C_7$-$C_{12}$ branched or unbranched alkyl group.

The monoacyl glycerol can have a structure represented as follows:

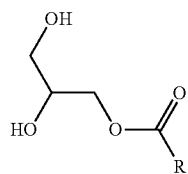

wherein R=$C_3$-$C_{18}$ branched or unbranched alkyl group or alkylene group. In some antimicrobial compositions, R=$C_5$-$C_{15}$ branched or unbranched alkyl group or alkylene group, or R=$C_6$-$C_{14}$ branched or unbranched alkyl group or alkylene group, or R=$C_7$-$C_{12}$ branched or unbranched alkyl group.

For each of the vicinal diols, when R is branched, the respective compound can exist as a racemic mixture of D,L components, as a pure enantiomer of D or L configuration, or as an enantiomer enriched mixture.

The antimicrobial composition can also include a metal ion chelating agent, a surfactant, or both. The antimicrobial composition can have a pH in the range 4.5-7.0 and an osmolality of 10-320 mOsm/kg. Where the antimicrobial composition is a solution, a water-soluble polymer can be added to increase solution viscosity and to prolong residence time of the antimicrobial composition on the surface of the wound. A hydrophobic fatty acid ester and a hydrophobic monoalkyl alcohol can be added to increase biocidal activity. Though fatty acid esters and hydrophobic monoalkyl alcohols are normally water insoluble or difficultly water soluble, they can be solubilized in the antimicrobial compositions described herein using a surfactant in conjunction with a hydrophobic glycol or hydrophobic glycerol.

The aqueous antimicrobial compositions described herein can include biocidal polymeric biguanides at a concentration ranging from 0.05 wt % (500 ppm) to 1 weight ° A. (10,000 ppm), or ranging from 0.075 wt % (750 ppm) to 0.5 wt % (5,000 ppm), or ranging from 0.1 wt % (1,000 ppm) to 0.15 wt % (1,500 ppm). Bis(biguanides), such as alexidine and its salts and chlorhexidine and its salts, can also be added to the antimicrobial compositions in concentrations from 10 ppm (0.001 wt %) to 350 ppm (0:035 wt %).

The antimicrobial composition can include the biocidal monoalkyl glycol, glycerol alkyl ether, and monoacyl glycerol at a combined concentration of from 0.05 wt % (500 ppm) to 4 wt % (4,000 ppm), or from 0.1 wt % (1,000 ppm) to 1 wt % (10,000 ppm), or from 0.4 wt % (4,000 ppm) to 0.6 wt % (6,000 ppm). The monoalkyl glycol, glycerol alkyl ether, and monoacyl glycerol can be hydrophobic because of the length of the R substituents. As used herein, hydrophobic refers to repelling water, being insoluble or relatively insoluble in water, and lacking an affinity for water. Hydrophobic compounds with hydrophilic substituents, such as vicinal diols, may form emulsions in water, with or without added surfactant.

When the antimicrobial composition is applied to a substrate or medical device in either the hydrated or dried form, the mixture can contain polymeric biguanides, at a concentration of from 0.05 wt % (500 ppm) to 1.5 weight % (15,000 ppm), or from 0.075 wt % (750 ppm) to 0.75 wt % (7,500 ppm), or from 0.1 wt % (1,000 ppm) to 0.5 wt % (5,000 ppm), and antimicrobial glycols and antimicrobial glycerols of a concentration of from 0.05 wt % (500 ppm) to 6 wt % (60,000 ppm), or from 0.1 wt % (1,000 ppm) to 1 wt % (10,000 ppm), or from 0.3 wt % (3,000 ppm) to 0.6 wt % (6,000 ppm).

The ratio of polymeric biguanide to vicinal diols (i.e., monoalkyl glycol, glycerol alkyl ether, and monoacyl glycerol combined) in the antimicrobial composition—whether hydrated or dried—can range from 1:0.05 to 1:500, or from 1:0.5 to 1:100, or from 1:0.75 to 1:75, or from 1:1 to 1:50, wherein the minimum concentration of polymeric biguanide is 0.02 wt % (200 ppm).

Any of the antimicrobial compositions described herein can be aqueous compositions. As used herein, "aqueous" compositions refer to a spectrum of water-based solutions including, but not limited to, homogeneous solutions in water with solubilized components, emulsified solutions in water stabilized by surfactants or hydrophilic polymers, and viscous or gelled homogeneous or emulsified solutions in water.

When present, the surfactant can be present at a concentration of from 0.1 wt % (1,000 ppm) to 4 wt % (40,000 ppm), or from 0.75 wt % (7,500 ppm) to 3 wt % (30,000 ppm), or from 1 wt % (10,000 ppm) to 2 wt % (20,000 ppm). The surfactant lowers the surface tension of the solution, facilitating wetting of a wound surface (or any surface) for enhanced activity of the biocidal agent and for assistance with debridement.

When present, the chelating agent can be present at a concentration of from 0.01 wt % (100 ppm) to 1 wt % (10,000 ppm), or from 0.025 wt % (250 ppm) to 0.5 wt % (5,000 ppm), or from 0.05 wt %, (500 ppm) to 0.2 wt % (2,000 ppm). It is believed that the chelating agent enhances biocidal activity by removing multivalent metal ions from microbial surfaces, as well as, potentially facilitating wound healing by deactivating matrix metalloproteases to enhance tissue regeneration.

Some preferred antimicrobial agents include polymeric biguanides and polymeric bis(biguanides). Optionally, at least one low molecular weight bis(biguanide) can be added as an additional antimicrobial agent. Combinations of antimicrobial biguanides may enhance efficacy against the number and type of pathogenic microbial species.

A preferred polymeric biguanide is poly(hexamethylene biguanide), commercially available from Arch Chemicals, Inc., Smyrna, Ga. under the trademark Cosmocil™ CQ. Poly(hexamethylene biguanide)polymers are also referred to as poly(hexamethylene biguanide) (PHMB), poly(hexamethylene bisbiguanide) (PHMB), poly(hexamethylene guanide) (PHMB), poly(aminopropyl biguanide) (PAPB), poly[aminopropyl bis(biguanide)] (PAPB), polyhexanide and poly(iminoimidocarbonyl)iminohexamethylene hydrochloride; however, PHMB is the preferred abbreviation for this biocidal polymer. PHMB is a broad spectrum antimicrobial and has been used in contact lens multipurpose solutions, wound rinsing solutions, wound dressings, perioperative cleansing products, mouthwashes, surface disinfectant, food disinfectant, veterinary applications, cosmetic preservative, paper preservative, secondary oil recovery disinfectant, industrial water treatment, and in swimming pool cleaners. It is normally obtained commercially in the hydrochloride form in water. Low molecular weight bis(biguanides) for antimicrobial activity are described in U.S. Pat. No. 4,670,592, the entirety of which is incorporated herein by reference. Preferred low molecular weight bis(biguanides) are alexidine (ALEX) and chlorhexidine (CHG), with alexidine being most preferred. Alexidine often exists in the dihydrochloride form while chlorhexidine is often in its gluconate form a Alexidine dihydrochloride is available from Toronto Research Chemicals, Inc., Toronto, Ontario, Canada. Alexidine is also listed chemically as 1,1'-hexamethylenebis[5-(2-ethylhexyl)biguanide] dihydrochloride. Chlorhexidine gluconate is available from Sigma Life Science, Sigma-Aldrich Corp., St. Louis, Mo. USA. Chlorhexidine gluconate is also listed chemically as 1,1'-hexamethylenebis[5-(p-chlorophenyl)biguanide]gluconate. Chlorhexidine has been used in many biomedical applications, while alexidine has been used primarily in mouthwash and in contact lens solutions.

Biguanides are described in U.S. Pat. Nos. 3,428,576, 4,670,592, 4,758,595 and 5,990,174, which are incorporated herein by reference in their entirety. Biguanide salts can be gluconates, nitrates, acetates, phosphates, sulfates, halides and the like. The preferred biguanides due to their ready commercial availability and superior biocidal effectiveness are poly(hexamethylene biguanide) hydrochloride (PHMB) and alexidine dihydrochloride (ALEX).

Other antimicrobial polymers can also be added, such as polyquaternium 1, polyquaternium 6, polyquaternium 10, cationic guar, and water-soluble derivatives of chitosan.

The antimicrobial composition can also include at least one vicinal diol selected from hydrophobic monoalkyl glycol, hydrophobic glycerol alkyl ethers, hydrophobic monoacyl glycerols and combinations thereof. In addition to being branched or unbranched, these compounds can either be saturated or unsaturated.

One or more hydrophobic monoalkyl or monoalkylene alcohol can also be added to the antimicrobial composition to enhance biocidal activity. The monoalkyl alcohol can include a single hydroxyl group, i.e., is not a polyol. The monoalkyl alcohol can be solubilized by a surfactant. Preferred hydrophobic monoalkyl alcohols include, but are not limited to, 1-octanol, 1-nonanol, 1-decanol, 1-undecanol, 1-dodecanol, 1-tridecanol, 1-tetradecanol, 1-pentadecanol, 1-hexadecanol, 1-heptadecanol, 1-octadecanol, and 3,7,11,15-tetramethyl-2-hexadecen-1-ol (phytol). Long-chain alcohols with fewer than seven carbon atoms and more than 18 carbon atoms are not preferred. The antimicrobial composition can be free of short chain monohydric alcohols, such as methanol, ethanol, propanol, butanol, pentanol, hexanol, heptanol, isomers thereof, or any combination thereof. More preferred monoalkyl or monoalkylene alcohols are 1-dodecanol, 1-tridecanol, and 3,7,11,15-tetramethyl-2-hexadecen-1-ol (phytol).

Antimicrobial sugar esters can also be added to increase biocidal activity. Sugar esters are effective for *Bacillus* sp., *Lactobacillus plantarum*, *Escherichia coli*, and various members of *Clostridium*. Such sugar esters comprise sucrose monocaprylate, sucrose monolaurate, sucrose monomyristate and sucrose monopalmitate.

Exemplary monoalkyl glycols include, but are not limited to, 1,2-propanediol (propylene glycol), 1,2-butanediol, 1,2-pentanediol, 1,2-hexanediol, 1,2-heptanediol, 1,2-octanediol (caprylyl glycol), 1,2-nonanediol, 1,2-decanediol, 1,2-undecanediol, 1,2-dodecanediol, 1,2-tridecanediol, 1,2-tetradecanediol, 1,2-pentadecanediol, 1,2-hexadecanediol, 1,2-heptadecanediol and 1,2-octadecanediol. Non-vicinal glycols can also be added to enhance biocidal activity. Exemplary, non-vicinal glycols include, but are not limited to, 2-methyl-2,4-pentanediol, 1,3-butanediol, diethylene glycol, triethylene glycol, and glycol bis(hydroxyethyl)ether.

Exemplary glycerol alkyl ethers include, but are not limited to, 1-O-heptylglycerol, 1-O-octylglycerol, 1-O-nonylglycerol, 1-O-decylglycerol, 1-O-undecylglycerol, 1-O-dodecylglycerol, 1-O-tridecylglycerol, 1-O-tetradecylglycerol, 1-O-pentadecylglycerol, 1-O-hexadecylglycerol (chimyl alcohol), 1-O-heptadecylglycerol, 1-O-octadecylglycerol (batyl alcohol), 1-O-octadec-9-enyl glycerol (selachyl alcohol), glycerol 1-(2-ethylhexyl)ether (also known as octoxyglycerin, 2-ethylhexyl glycerin, 3-(2-ethylhexyloxy)propane-1,2-diol, and Sensiva® SC 50), glycerol 1-heptyl ether, glycerol 1-octyl ether, glycerol 1-decyl ether, and glycerol 1-dodecyl ether, glycerol 1-tridecyl ether, glycerol 1-tetradecyl ether, glycerol 1-pentadecyl ether, glycerol 1-hexadecyl ether and glycerol 1-octadecyl ether.

Exemplary monoacyl glycerols include, but are not limited to, 1-O-decanoylglycerol (monocaprin), 1-O-undecanoylglycerol, 1-O-undecenoylglycerol, 1-O-dodecanoylglycerol (monolaurin, also called glycerol monolaurate and Lauricidin®), 1-O-tridecanoylglycerol, 1-O-tetradecanoylglycerol (monomyristin), 1-O-pentadecanoylglycerol, 1-O-hexadecanoylglycerol, 1-O-heptadecanoylglycerol, and 1-O-octanoylglycerol (monocaprylin). In general, glycerols substituted in the 1-O-position are more preferred than those substituted in the 2-O-position, or disubstituted in the 1-O and 2-O positions.

The Sensiva® SC 10 Multifunctional Cosmetic Ingredient available from Schülke & Mayr, which includes both 1,2-octanediol (a monoalkyl glycol) and 2-ethylhexyl glycerin (glycerol 1-(2-ethylhexyl)ether) (a monoalkyl glycerol), is an exemplary vicinal diol composition for use in the antimicrobial compositions described herein. Sensiva® SC 10 is reported to combine the excellent skin care and deodorizing properties of 2-ethylhexylglycerin (Sensiva® SC 50) with the moisturizing and antimicrobial properties of caprylyl glycol. Additionally, the vicinal diols can contribute to the antimicrobial stability of cosmetic formulations. Vicinal diols can also be used to improve the efficacy of traditional cosmetic preservatives, such as parabens or phenoxyethanol (Schülke & Mayr, Sensiva® SC 10 Multifunctional Cosmetic Ingredient).

Sensiva® SC 50 reliably inhibits the Gram positive odor-causing bacteria on the skin and is used in deodorant formulations. It is reported to boost the efficacy of traditional preservatives. In addition, screening tests with Sensiva® SC 10 have shown that it reliably inhibits the growth and multiplication of Gram positive odor causing bacteria, while at the same time it does not affect beneficial skin flora. The antimicrobial efficacy of methylparaben preservative is accelerated by Sensiva® SC 10 in reduction of cfu/ml for *Aspergillus niger* (ATCC 6275), *Candida albicans* (ATCC 10231), *Staphylococcus aureus* (ATCC 6538), *Pseudomonas aeruginosa* (ATCC 15442) and *Escherichia coli* (ATCC 11229). The compositions studied were 0.2 (wt) % methylparaben, 1.0 (wt) % (10,000 ppm) Sensiva® SC 10, and a combination of 0.2 (wt) % methylparaben and 1.0 (wt) % Sensiva® SC 10. The recommended preservative use concentration for Sensiva® SC 10 by Schülke & Mayr is 0.5 (5,000 ppm) to 2.0% (20,000 ppm).

Since the antimicrobial monoalkyl vicinal diols of this invention have adjacent hydrophilic —OH groups, but often with low or negligible water solubility, it is preferred that a surfactant be added to aid in solution compatibilization and homogeneity of these compounds.

The antimicrobial compositions can include one or more additional surfactants to effect surface cleaning, particularly for debridement of wounds. Suitable surfactants include, but are not limited to, cationic, anionic, nonionic, amphoteric and ampholytic surfactants. Preferred surfactants are nonionic and amphoteric surfactants. The surfactants can have an HLB (hydrophilic-lipophilic balance) value of 18-30 in order to maintain the biocidal activity of the antimicrobial agents, while facilitating a non-cytotoxic solution.

Suitable nonionic surfactants include the ethylene oxide/propylene oxide block copolymers of poloxamers, reverse poloxamers, poloxamines, and reverse poloxamines. Poloxamers and poloxamines are preferred, and poloxamers are most preferred. Poloxamers and poloxamines are available from BASF Corp. under the trade names of Pluronic® and Tetronic®.

Suitable Pluronic surfactants comprise but are not limited to Pluronic F38 having a HLB of 31 and average molecular weight (AMW) of 4,700, Pluronic F68 having a HLB of 29 and AMW of 8,400, Pluronic 68LF having a HLB of 26 and AMW or 7,700, Pluronic F77 having a HLB of 25 and AMW of 6,600, Pluronic F87 having a HLB of 24 and AMW of 7,700, Pluronic F88 having a HLB of 28 and AMW or 11,400, Pluronic F98 having a HLB of 28 and AMW of 13,000, Pluronic F108 having a HLB of 27 and AMW of 14,600, Pluronic F127 (also known as Poloxamer 407) having a HLB of 18-23 and AMW of 12,600, and Pluronic L35 having a HLB of 19 and AMW of 1,900.

Another class of surfactant is that of the diamino block copolymers of ethylene oxide and propylene oxide sold by BASF Corp. under the trade name Tetronic®. An exemplary surfactant of this type is Tetronic 1107 (also known as Poloxamine 1107).

In addition to the above, other surfactants may be added, such as for example polyethylene glycol esters of fatty acids, e.g., coconut, polysorbate, polyoxyethylene or polyoxypropylene ethers of higher alkanes ($C_{12}$-$C_{18}$), polysorbate 20 available under the trademark Tween 20, polyoxyethylene (23) lauryl ether available under the trademark Brij 35, polyoxyethylene (40) stearate available under the trademark Myrj 52, and polyoxyethylene (25) propylene glycol stearate available under the trademark Atlas G 2612, all available by Akzo Nobel, Chicago, Ill. Other neutral surfactants include nonylphenol ethoxylates such as nonylphenol ethoxylates, Triton X-100, Brij surfactants of polyoxyethylene vegetable-based fatty ethers, Tween 80, decyl glucoside, and lauryl glucoside.

Amphoteric surfactants suitable for use in antimicrobial compositions according to the present invention include materials of the type offered commercially under the trademark Miranol (Rhodia). Another useful class of amphoteric surfactants is exemplified by cocoamidopropyl betaine, commercially available from various sources.

Examples of suitable tonicity adjusting agents include, but are not limited to: sodium chloride and potassium chloride, glycerin, propylene glycol, mannitol and sorbitol. These agents are typically used individually in amounts ranging from about 0.01 to 2.5% (w/v) and preferably, from about 0.05 to about 1.5% (w/v). Preferably, the tonicity agent will be employed in an amount to provide a final osmotic value of from 10 to 320 mOsm/kg and more preferably between about 200 to about 300 mOsm/kg, and most preferably between about 260 to about 290 mOsm/Kg. Sodium chloride is most preferred to adjust the antimicrobial composition tonicity.

The pH of the antimicrobial composition is adjusted to between 4.5 to 7.0, with pH 5.0 to pH 6.5 being more preferred, and pH 5.5 to 6.0 being most preferred. The role of wound bed pH is of fundamental importance during the healing of chronic wounds, and prolonged acidification of the wound bed has been shown to increase the healing rate in chronic venous leg ulcers (Wilson I. A. I., Henry M., Quill R. D., and Byrne P. J., VASA 1979, vol. 8, pages 339-342). The principal explanation for the mechanism of interaction between the acidic wound bed and the wound healing process is related to the potential to increase tissue oxygen availability through oxygen dissociation and to reduce the histotoxicity of bacterial end products, thus stimulating the wound's healing process.

Suitable buffers to adjust pH can include sodium citrate, potassium citrate, citric acid, sodium dihydrogen phosphate, disodium monophosphate, boric acid, sodium borate, tartrate, phthalate, succinate, acetate, propionate, maleate salts, tris (hydroxymethyl)aminomethane, amino alcohol buffers, and Good buffers (such as ACES, PIPES, and MOPOSO), and mixtures thereof. One or more buffers can be added to antimicrobial compositions of the present invention in amounts ranging between approximately 0.01 to 2.0 weight percent by volume, but more preferably between approximately 0.05 to 0.5 weight percent by volume.

Additionally, the pH of the antimicrobial composition can be adjusted by the combination of ethylenediaminetetracetic acid disodium and trisodium salt chelating agents, with this method being most preferred.

Emollients/moisturizers and humectants can be added to the antimicrobial formulation to provide a more soothing antimicrobial composition. Emollients/moisturizers function by forming an oily layer on the top of the skin that traps water in the skin. Petrolatum, lanolin, mineral oil, dimethicone, and siloxy compounds are common emollients. Other emollients include isopropyl palmitate, isopropyl myristate, isopropyl isostearate, isostearyl isostearate, diisopropyl sebacate, propylene dipelargonate, 2-ethylhexyl isononoate, 2-ethylhexyl stearate, cetyl lactate, lauryl lactate, isopropyl lanolate, 2-ethylhexyl salicylate, cetyl myristate, oleyl myristate, oleyl stearate, oleyl oleate, hexyl laurate, and isohexyl laurate, lanolin, olive oil, cocoa butter, shea butter, octyldodecanol, hexyldecanolc dicaprylylether and decyl oleate.

Humectants include glycerin, lecithin, 1,2-propylene glycol, dipropylene glycol, polyethylene glycol, 1,3-butylene glycol, and 1,2,6-hexanetriol. Humectants function by drawing water into the outer layer of skin.

Anti-inflammatory agents can also be added, such as water soluble derivatives of aspirin, vitamin C, methylsulfonylmethane, tea tree oil, and non-steroidal anti-inflammatory drugs.

The water-insoluble additive compounds can be solubilized using a surfactant, particularly in combination with at least one antimicrobial hydrophobic monoalkyl vicinal diol, antimicrobial hydrophobic monoalkyl glycerol and antimicrobial hydrophobic monoacyl glycerol.

It is often desirable to include water-soluble viscosity builders in the antimicrobial compositions of the present invention. Because of their demulcent effect and possible hydrophobic interactions with biological tissue, water-soluble polymers have a tendency to enhance the interaction with a wound by means of a hydrated film on the wound surface. Because of this behavior, such water-soluble polymers can increase the residence time of the antimicrobial composition or gel on a wound.

Water-soluble viscosity builders useful herein include, but are not limited to, methylcellulose, hydroxyethylcellulose, hydroxypropylcellulose, hydroxypropylmethylcellulose, carboxymethylcellulose, polyquaternium-1, polyquaternium-6, polyquaternium-10, guar, hydroxypropylguar, hydroxypropylmethylguar, cationic guar, carboxymethylguar, hydroxymethylchitosan, hydroxypropylchitosan, carboxymethylchitosan, N-[(2-hydroxy-3-trimethylammonium)propyl]chitosan chloride, water-soluble chitosan, hyaluronic acid and its salts, chondroitin sulfate, heparin, dermatan sulfate, amylose, amylopectin, pectin, locust bean gum, alginate, dextran, carrageenan, xanthan gum, gellan gum, scleroglucan, schizophyllan, gum arabic, gum ghatti, gum karaya, gum tragacanth, pectins, starch and its modifications, tamarind gum, poly(vinyl alcohol), poly(ethylene oxide), poly(ethylene glycol), poly(methyl vinyl ether), polyacrylamide, poly(N,N-dimethylacrylamide), poly(N-vinylacetamide), poly(N-vinylformamide), poly(2-hydroxyethyl methacrylate), poly(glyceryl methacrylate), poly(N-vinylpyrrolidone), poly(dimethylaminoethyl methacrylate), poly(dimethylaminopropyl acrylamide), polyvinylamine, poly(N-isopropylacrylamide) and poly(N-vinylcaprolactam), the latter two hydrated below their Lower Critical Solution Temperatures, and the like, and combinations thereof. Such viscosity builders may be employed in amounts ranging from about 0.01 to about 10.0 weight percent for preparation of free flowing antimicrobial compositions to viscous gels.

If anionic hydrophilic polymers are utilized for enhancing viscosity, the overall polymer negative charge may electrostatically attract and accumulate the cationic biguanide biocide and a greater concentration of biguanide will then be needed to provide biocidal efficacy comparable to the utilization of a neutral or cationic water-soluble polymer. Thus, preferred water soluble polymers are neutral in charge, such as hydroxyethylcellulose, hydroxypropylcellulose, hydroxypropylmethylcellulose, guar, hydroxypropylguar, hydroxypropylmethylguar, poly(ethylene oxide), and poly(N-vinylpyrrolidone), or cationic in charge, such as cationic chitosans, cationic cellulosics, and cationic guar. Chitosan polymers may also enhance the antimicrobial behavior of the antimicrobial composition. More preferred hydrophilic polymers comprise hydroxypropylmethylcellulose, hydroxypropylcellulose, hydroxypropylguar, hydroxymethylchitosan, poly(ethylene oxide), N-[(2-hydroxy-3-trimethylammonium)propyl]chitosan chloride, with hydroxymethylpropylcellulose being most preferred.

Chelating agents enhance the susceptibility of bacteria and other organisms to the biocidal effects of the antimicrobial agent, thus rendering a wound care solution or device containing a chelating agent more effective in combating infection. Additionally, chelating agents deactivate matrix metalloproteases (MMPs), enzymes that can impede tissue formation and healing by breaking down collagen. MMPs are often found at elevated levels in chronic wounds. Chelating agents bind to zinc ions, which are necessary for MMP activity, disrupting the MMP, causing deactivation, and thus facilitating healing.

The chelating agent is selected from any compound that is able to sequester monovalent or polyvalent metal ions, such as sodium, lithium, rubidium, cesium, calcium, magnesium, barium, cerium, cobalt, copper, iron, manganese, nickel, strontium or zinc, and is pharmaceutically or veterinarily acceptable. The outermost surface of bacterial cells universally carries a net negative charge, which is usually stabilized by divalent cations such as $Mg^{+2}$ and $Ca^{+2}$. This is associated with the teichoic acid and polysaccharide elements of Gram-positive bacteria, the lipopolysaccharide of Gram-negative bacteria, and the cytoplasmic membrane itself. Thus, the chelating agent aids in destabilizing microorganisms. Additionally, the chelating agent may deactivate matrix metalloproteases, such as in inflammatory wounds, facilitating collagen development.

Suitable chelating agents comprise, but are not limited to, aminocarboxylic acids, ethylenediaminetetraacetic acid (EDTA), nitrilotriacetic acid, nitrilotripropionic acid, diethylenetriaminepentaacetic acid, 2-hydroxyethylethylenediaminetriacetic acid, 1,6-diaminohexamethylenetetraacetic acid, 1,2-diaminocyclohexanetetraacetic acid, O,O'-bis(2-aminoethypethyleneglycoltetraacetic acid, 1,3-diaminopropanetetraacetic acid, N,N'-bis(2-hydroxybenzyl)ethylenediamine-N,N'-diacetic acid, ethylenediamine-N,N'-diacetic acid, ethylenediamine-N,N'-dipropionic acid, triethylenetetraaminehexaacetic acid, ethylenediamine-N,N'-bis(methylenephosphonic acid), iminodiacetic acid, N,N-bis(2-hydroxyethyl)glycine, 1,3-diamino-2-hydroxypropanetetraacetic acid, 1,2-diaminopropanetetraacetic acid, ethylenediaminetetrakis (methylenephosphonic acid), N-(2-hydroxyethyl) iminodiacetic acid and biphosphonates such as editronate, and salts thereof. Suitable chelating agents include for example but are not limited to hydroxyalkylphosphonates as disclosed in U.S. Pat. No. 5,858,937, specifically the tetrasodium salt of 1-hydroxyethylidene-1,1-diphosphonic acid, also referred to as tetrasodium etidronate, commercially available from Monsanto Company as DeQuest 2016 diphosphonic acid sodium salt or phosphonate.

Especially preferred chelating agents are mixed salts of EDTA such as disodium, trisodium, tetrasodium, dipotassium, tripotassium, tetrapotassium, lithium, dilithium, ammonium, diammonium, triammonium, tetraammonium, calcium and calcium-disodium, more preferably disodium, trisodium or tetrasodium salts of EDTA, and most preferably disodium EDTA and trisodium EDTA.

The concentration of chelating agent can range from 0.01 weight % to 1.0 weight %, or from 0.025 to 0.5 weight %, or from 0.05 to 0.15 weight %.

It is also possible to prepare the wound cleanser as an emulsion, a miniemulsion, a microemulsion or an inverse emulsion utilizing the surfactant to solublilize an active, normally water insoluble or difficult to solubilize component. The solubilization of organic and inorganic species could include antimicrobials, antibiotics, silver salts and silver nanoparticles, antibacterial agents, antifungal agents, antiviral agents, antiprotozoal agents, essential oils, analgesics, protease inhibitors, antiallergenics, anti-inflammatories, vasoconstrictors, vasodilators, anticlotting agents, hormones, peptides, nucleic acids, saccharides, lipids, glycolipids, glycoproteins, endocrine hormones, growth hormones, growth factors, heat shock proteins, immunological response modifiers, anti-cancer agents, cytokines, and mixtures thereof, as well as organic solvents that provide increased oxygen to ischemic wounds. Of significance are the addition of organic solvents, such as siloxanes and fluorocarbons, which increase oxygen solubility and transport. Of particular significance is the use of a volatile, non-burning, non-stinging, non-sensitizing, siloxane solvent of hexamethyldisiloxane (HMDS). The emulsion is prepared by slowly adding the HMDS to the composite wound care composition up to the concentration wherein phase separation occurs between the organic solvent and the emulsified solution.

Essential oils can also be added to the formulation as fragrance or aromatic agents, and/or as antimicrobial agents, including thymol, menthol, sandalwood, camphor, cardamom, cinnamon, jasmine, lavender, geranium, juniper, menthol, pine, lemon, rose, eucalyptus, clove, orange, mint, linalool, spearmint, peppermint, lemongrass, bergamot, citronella, cypress, nutmeg, spruce, tea tree, wintergreen (methyl salicylate), vanilla, and the like. More preferred essential oils include thymol, sandalwood oil, wintergreen oil and eucalyptol for antimicrobial properties and pine oil for fragrance. Thymol and sandalwood oil are the most preferred essential oils.

In topical applications, the antimicrobial composition product may be delivered in different forms. Exemplary forms include, but not limited to, liquids, creams, foams, lotions, gels and aerosols. The antimicrobial composition can also be imbibed by swabs, cloth, sponges, foams, wound dressing materials and non-woven and paper products, such as paper towels and wipes. Topical formulations of the subject antimicrobial compositions may additionally comprise organic solvents, emulsifiers, gelling agents, moisturizers, stabilizers, time release agents, dyes, perfumes, and like components commonly employed in formulations for topical administration.

The antimicrobial compositions or gels may also be added to catheters in a hydrated or dried form to provide a coating that can be inserted into a body in order to prevent biofilm attachment to the catheter.

Alternatively, the antimicrobial composition may be added to a solid or porous support and dried, such as a polymeric foam, a polymer film, a woven, knitted or nonwoven material, and then applied directly to a wound. In this case the polymeric foam may also absorb wound exudate, creating a hydrated environment for controlled release of synergistic biguanide activity with the antimicrobial monoalkyl vicinal diol on the wound surface. Such foam wound dressings can comprise up to 1.0 weight % biguanide. Foam dressings of this type would be effective against biofilms such as *Pseudomonas aeruginosa*, methicillin-resistant *Staphylococcus aureus* and vancomycin-resistant *Enterococci*.

Furthermore, the above compositions may be used in dentistry to control or eradicate biofilm populations in oral applications, such as for gingivitis. In addition, the above compositions may be utilized for biofilms in the middle ear that have been found in chronic otitis media.

The above compositions may be used to disinfect surfaces, such as bedding, surgery tables, tubing, and reusable medical equipment.

EXAMPLES

Antimicrobial solutions containing PHMB are well recognized for their antimicrobial behavior and for their contributions to wound management. Recently, a commercial product, Protonsan® Wound Irrigation Solution with PHMB (poly (hexamethylene biguanide), polyhexanide), was introduced by B. Braun into the U.S. and Europe markets for moistening and cleansing of acute and chronic wounds or burns to help reduce necrotic burden, control exudate and remove foreign material. It can be used on colonized, critically colonized, and infected wounds. Additionally, Prontosan® Wound Irrigation Solution has been reported to decontaminate encrusted, contaminated and chronic skin wounds, and can have a dramatic influence of the quality of life for such patients (Horrocks A., Br. J. Nurs., 2006 Dec. 14-2007 Jan. 10; 15(22):1222, 1224-8). Because Prontosan® Wound Irrigation Solution contains PHMB, it is used as a positive control for the biofilm reduction and elimination examples in this invention.

The following examples serve to illustrate the invention without limiting it thereby. It will be understood that variations and modifications can be made without departing from the spirit and scope of the invention.

The antimicrobial agents, surfactant, viscosity enhancing agent, chelating agents and skin care and deodorizing agent used in these examples include:
PHMB: (Poly(hexamethylene biguanide)), Cosmocil™ CQ, Arch Chemical lot 11RC116995).
ALEX: (Alexidine Dihydrochloride), Toronto Research Chemicals, lot 4-WG-119-2.
CHG: (Chlorhexidine gluconate), Spectrum Chemicals, lot ZQ1023.
P-407: (Poloxamer 407, Pluronic F127), Spectrum Chemicals, lot 1AD0265.
TW 80: (Tween 80, Polysorbate 80), Spectrum Chemicals, lot XF0356
HPMC: (Hydroxypropylmethylcellulose, Hypromellose), Spectrum Chemicals, lot 1AC0441, 2% solution viscosity=50 mPa·s.
EDTA-2: (Ethylenediaminetetraacetic acid disodium salt), Spectrum Chemicals, lot 1AE0430.
EDTA-3: (Ethylenediaminetetraacetic acid trisodium salt), Spectrum Chemicals, lot YL0044.
SC 50: (Sensiva® SC 50, Glycerol 1-(2-ethylhexyl)ether), Schülke & Mayr, lot 1179743.
SC 10: (Sensiva® SC 10, 1,2-Dihydroxyoctane), Schülke & Mayr, lot 1178933.
GML: (Glycerol Monolaurate, Lauricidin®), Med-Chem Laboratories, lot 4010608422.
SAN: (Sandalwood oil, East Indian Sandalwood tree, *Santalum album*), ViroX is Corporation.
Sodium Chloride: Spectrum Chemical, lot 1AA0110.
Water: (Purified, USP), Ricca Chemical Company, lot 1102304.

Since the Prontosan® solution contains PHMB at 0.1 wt % (1,000 ppm) and a surfactant, undecylenamidopropyl betaine (0.1 wt %, 1,000 ppm), this aqueous solution was used as a positive control, with saline as the negative control, in comparing PHMB containing solutions of this invention at 1000 ppm (0.1 wt %) and 1500 ppm (0.15 wt %) with the addition of Sensiva® SC 50 at 0.3 wt % (3,000 ppm) and Sensiva® SC 10 at 0.1 wt % (1,000 ppm) for their efficacy against biofilms of *Pseudomonas aeruginosa, Staphylococcus aureus,* and *Candida albicans*. Additional ingredients included alexidine (ALEX) and chlorhexidine (CHG) bis(biguanides), EDTA-2Na and EDTA-3Na chelating agents, and pH adjustment by ethylenediaminetetraacetic acid disodium and trisodium salts, Poloxamer 407 surfactant, and hydroxypropylmethylcellulose viscosity enhancer, with the osmolality adjusted by sodium chloride.

In Table 1 are listed fifteen antimicrobial compositions that were prepared for comparison against the controls.

pH 5.5 and 6). The osmolality was either 262 or 280 mOsm/kg, forming mildly hypotonic solutions. The antimicrobial compositions were undiluted and compared for their effects on biofilm growth and relative kill efficacy vs. controls.

Protonsan® positive control was determined to have a pH of 6 and an osmolality of 11 mOsm/Kg.

The following two bacterial biofilm species were tested: *Pseudomonas aeruginosa* (ATCC strain 27853, Gram negative bacteria) and methicillin-resistant *Staphylococcus aureus* (MRSA; ATCC strain 700699, Gram positive bacteria). For fungi, the biofilm of *Candida albicans* (ATCC strain

TABLE 1

Solutions for Biofilm Studies

| Solution | PHMB ppm | ALEX ppm | CHG ppm | EDTA-2Na wt % | EDTA-3Na wt % | P-407 wt % | HPMC wt % | SC50 wt % | SC10 wt % | SAN wt % | Osmolality mOsm/kg | pH |
|---|---|---|---|---|---|---|---|---|---|---|---|---|
| 1 | 1000 | 10 | 0 | 0.1 | 0 | 1 | 0.2 | 0 | 0 | 0 | 280 | 4.9 |
| 2 | 1000 | 10 | 0 | 0.5 | 0.55 | 1 | 0.2 | 0 | 0 | 0 | 262 | 6.0 |
| 3 | 1000 | 0 | 0 | 0.1 | 0.060 | 1 | 0.2 | 0 | 0 | 0 | 262 | 6.0 |
| 4 | 1000 | 0 | 0 | 0.05 | 0.015 | 2 | 0.2 | 0.3 | 0.1 | 0 | 280 | 5.5 |
| 5 | 1000 | 0 | 0 | 0.05 | 0.025 | 2 | 0.2 | 0.3 | 0.1 | 0.125 | 280 | 5.5 |
| 6 | 1000 | 10 | 0 | 0.05 | 0.025 | 2 | 0.2 | 0.3 | 0.1 | 0 | 280 | 5.5 |
| 7 | 1000 | 10 | 0 | 0.5 | 0.025 | 2 | 0.2 | 0.3 | 0.1 | ≤0.125 | 280 | 5.5 |
| 8 | 1000 | 0 | 200 | 0.05 | 0.025 | 2 | 0.2 | 0.3 | 0.1 | 0 | 280 | 5.5 |
| 9 | 1000 | 0 | 200 | 0.05 | 0.025 | 2 | 0.2 | 0.3 | 0.1 | 0 | 280 | 5.5 |
| 10 | 1500 | 0 | 0 | 0.1 | 0.035 | 2 | 0.2 | 0 | 0 | 0 | 262 | 5.5 |
| 11 | 1500 | 10 | 0 | 0.1 | 0.045 | 2 | 0.2 | 0 | 0 | 0 | 262 | 5.5 |
| 12 | 1500 | 0 | 0 | 0.1 | 0.045 | 2 | 0.2 | 0.3 | 0.1 | 0 | 262 | 5.5 |
| 13 | 1500 | 0 | 0 | 0.1 | 0.045 | 2 | 0.2 | 0.3 | 0.1 | 0.125 | 262 | 5.5 |
| 14 | 1500 | 10 | 0 | 0.1 | 0.045 | 2 | 0.2 | 0.3 | 0.1 | ≤0.125 | 262 | 5.5 |
| 15 | 1500 | 0 | 200 | 0.1 | 0.045 | 2 | 0.2 | 0.3 | 0.1 | ≤0.125 | 262 | 5.5 |

Biofilms were established and assayed as follows. For each organism, 96-peg MBEC™ pegs were placed in a 96 well plate with 100 µl of 0.1 OD 600 log phase bacterial culture per well. The biofilms were allowed to grow on the pegs for 36 to 48 hours. Excess bacteria were then rinsed in a 96 well plate with 200 µl/well of PBS for 10±1 minutes. The cells were then treated with the antimicrobial compositions and positive and negative controls in a 96 well plate at 200 µl per well for 8±2 min. The plates were then rinsed as above in a fresh plate. The pegs were then transferred to a neutralization plate containing 200 µl per well of Dey-Engley broth and lightly sonicated for 15 min to release the planktonic organisms associated with the pegs. After sonication, the peg plate was moved to a regrowth plate with 200 µl of Tryptic Soy Broth (TSB) and incubated for ~24 hours. The assay was completed by reading the absorbance at 600 nm in a Molecular Devices M2 microplate reader (*C. albicans* was also read at ~48 hours.)

The antimicrobial compositions contained poly(hexamethylene biguanide) hydrochloride (PHMB) biocide at either 1000 ppm (0.1 wt %) or 1500 ppm (0.15 wt %), with alexidine (ALEX) at 0 ppm or 10 ppm (0.001 wt %), with chlorhexidine digluconate (CHG) at 0 ppm or 200 ppm (0.02 wt %), with EDTA chelating agent at 0.05 wt % (500 ppm) or 0.1 wt % (1,000 ppm), with Poloxamer F127 (P-407) surfactant at 1 wt % (10,000 ppm) or 2 wt % (20,000 ppm), with HPMC viscosity enhancer at 0.2 wt % (2,000 ppm), with Sensiva® SC 50 (SC 50), an emollient and humectant that inhibits the growth of Gram positive odor causing bacteria, at 0 wt % to 0.3 wt % (3,000 ppm), with Sensiva® SC 10 (SC 10), an emollient and humectant with deodorizing and antimicrobial properties, at 0 wt % or 0.1 wt % (1,000 ppm), and with Sandalwood oil (SAN), an essential oil, at 0 wt % to 0.125 wt % (1,250 ppm). Additionally, pH was obtained by no added ingredients (i.e., pH 4.9) or by the addition of trisodium EDTA (EDTA-3Na) to disodium EDTA (EDTA-3Na) (i.e., 10231, yeast) was analyzed. All antimicrobial compositions were studied for regrowth over a 24 hour period. Solutions exposed to *Candida albicans* were also analyzed for regrowth at 48 hours because of the slower growth of this microorganism.

FIG. 1 is a graph of antimicrobial compositions 1-6 and 10-13 relative to a biofilm of *Pseudomonas aeruginosa*, ATCC 27853, based upon the absorbance of total bacteria at 600 nm before treatment with the antimicrobial compositions, followed by a 10 minute exposure to the solutions, and then by regrowth analysis after 24 hours. Graphs with no error bars signify no regrowth and are representative of the absorbance of dead microorganisms.

FIG. 1 shows that with the saline positive control, almost total regrowth occurs within 24 hours. For Prontosan®, which has PHMB at a concentration of 1000 ppm and a surfactant at 0.1 wt %, substantial regrowth also occurs within 24 hours. Similarly, for solutions 1, 2, 3, 10, and 11, which have neither vicinal diol constituent (Sensiva® SC 50 and Sensiva® SC 10), substantial regrowth also occurred. Comparing solutions 4 and 6, solutions that are similar other than the addition of 10 ppm alexidine to solution 6, it is seen that the addition of the alexidine had a negligible effect on the biocidal behavior in that a small error bar is noted in the optical density (OD) measurement. When there is no error bar in the measurement, the optical density measurement signifies the presence of exclusively dead microorganisms. In other words; the reading does not change because there is no regrowth of the microorganism. Solutions 4, 5, 6 and 12, 13 each contained 0.3 wt % Sensiva® SC 50 and 0.1 wt % Sensiva® SC 10. Each of these had the lowest optical density readings after 24 hours, indicating little or no regrowth of *Pseudomonas aeruginosa*. Solutions 4, 5, and 12 had no error bars, indicating total eradication of the *Pseudomonas aeruginosa* biofilm.

In comparing solutions 4, 5 and 6, each with 1000 ppm PHMB, solution 6 also contains 10 ppm alexidine while solutions 4 and 5 do not. Also, solution 5 also contains 0.125 wt % sandalwood oil, while solutions 4 and 6 do not. Solution 6 with alexidine has a slight error bar in its OD measurement, while solutions 4 and 5 do not. There is no significant difference in solutions 4 and 5, indicating that for the 24 hour time period of the test all bacteria were dead, and the addition of sandalwood oil could not be discerned.

Solutions 12 and 13 both contained 1500 ppm of PHMB, with solution 13 also containing 0.125 wt % sandalwood oil. The results show a slight error bar for solution 13, which indicates that solution 12 was more effective. Additionally, there was no significant difference between solutions 4, 5 and 12, indicating that for these formulations the combination of a polymeric biguanide at a concentration of at least 1000 ppm, with vicinal diol containing Sensiva® SC 50 and Sensiva® SC 10 at a concentration of 0.3 wt % and 0.1 wt %, respectively, effectively eliminates a *Pseudomonas aeruginosa* biofilm within a 10 minute exposure to the antimicrobial composition. The approximate two times difference in the total EDTA content between solution 12 and solutions 4 and 5 also indicated that there was no significant difference in the biocidal efficacy of these three solutions.

Combined with the results of the solutions without Sensiva® SC 50 and Sensiva® SC 10 present (solutions 1, 2, 3, 10 and 11), it is apparent that the combination of a polymeric biguanide with a vicinal diol, in particular monoalkyl glycerol (i.e., glycerol 1-(2-ethylhexyl)ether, also known as octoxyglycerin, 2-ethylhexyl glycerin, and Sensiva® SC 50) and a monoalkyl glycol (i.e., caprylyl glycol, 1,2-dihydroxyoctane; in combination with glycerol 1-(2-ethylhexyl)ether constitutes Sensiva® SC 10), gives an enhanced biocidal interaction against biofilms for solutions 4, 5 and 12. Since the Sensiva® products are reportedly effective against odor causing Gram positive bacteria, the superior results of the PHMB antimicrobial compositions with Sensiva® SC 50 and Sensiva® SC 10 against Gram negative *Pseudomonas aeruginosa* biofilms are quite surprising and further demonstrate the synergistic biocidal interaction between a polymeric biguanide and the vicinal diols.

Figure 2:
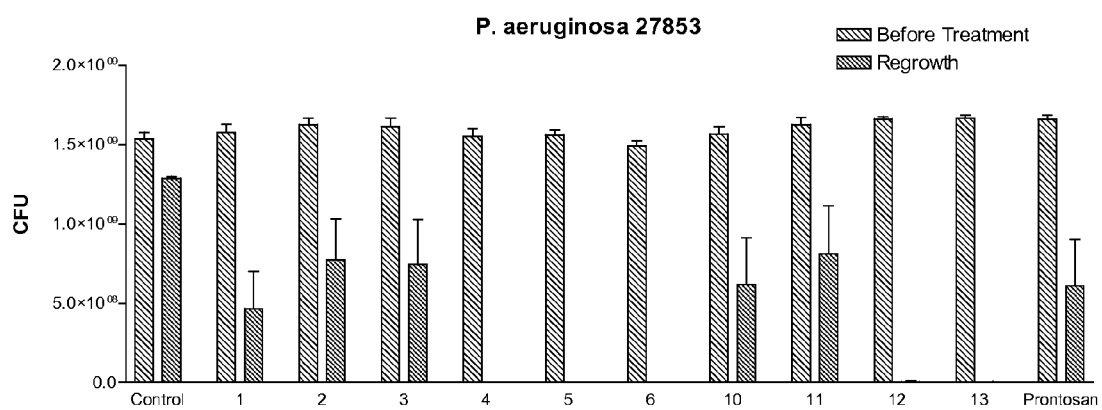
FIG. 2 is a graph showing *Pseudomonas aeruginosa* biofilm log kill graph for saline, PRONTOSAN® and solutions 1-6 and 11-13.

In FIG. 2 is a *Pseudomonas aeruginosa* log kill graph of CFU's before treatment with the antimicrobial compositions, followed by a 10 minute exposure to the solutions, and then by regrowth after 24 hours with for the same solutions of FIG. 1. That is, solutions 1-6 and 10-13, wherein the Optical Density measurements of FIG. 1 were converted to colony forming units (CFU) of *Pseudomonas aeruginosa* biofilm calculated as a conversion of the Absorbance at 600 nm (A600) to CFU based on a standard curve established for *Pseudomonas aeruginosa*. The limit of detection by the spectrophotometer used is 0.001 (Molecular Devices M2 microplate reader), which means the equivalent of $10^4$ cells/ml is the lower limit that can be measured. The debris from FIG. 1 was considered baseline. Thus, while the data in FIG. 2 can be interpreted as a kill of at least 8 log orders of *Pseudomonas aeruginosa*, the lower limit of quantitation indicates that the effective kill of the bacteria was approximately 5 log orders for the most efficacious solutions, i.e., solutions 4, 5, 6, 12 and 13, with solutions 4, 5 and 6 being the most effective antimicrobial compositions against *Pseudomonas aeruginosa* biofilm. Solutions 4, 5, 6, 12, and 13 were the only solutions with the combination of a polymeric biguanide and Sensiva® SC 50 and Sensiva® SC 10. Prontosan®, the positive control with a similar PHMB content to solutions 4, 5, and 6 but with neither Sensiva® SC 50 nor Sensiva® SC 10, had an effective kill of *Pseudomonas aeruginosa* biofilm of 1 log order. These results further demonstrate the synergistic interaction of the polymeric biguanide and a hydrophobic monoalkyl vicinal diol in reducing and eliminating a biofilm of *Pseudomonas aeruginosa*.

The log kill data is presented in Table 2. Solutions 4, 5, 6, 12, and 13 are reported as BLOQ, for values Below the Limit of Quantitation.

TABLE 2

*Pseudomonas aeruginosa* Biofilm Log Kill Tabulated Data for Solutions 1-6 and 11-13, with Saline and Prontosan ®.

| Solution | CFU Before Treatment | CFU 24 h Regrowth |
|---|---|---|
| Control | 1.54E+09 | 1.29E+09 |
| 1 | 1.58E+09 | 4.67E+08 |
| 2 | 1.63E+09 | 7.75E+08 |
| 3 | 1.61E+09 | 7.45E+08 |
| 4 | 1.55E+09 | BLOQ |
| 5 | 1.56E+09 | BLOQ |
| 6 | 1.49E+09 | BLOQ |
| 10 | 1.57E+09 | 6.20E+08 |
| 11 | 1.63E+09 | 8.11E+08 |
| 12 | 1.66E+09 | BLOQ |
| 13 | 1.67E+09 | BLOQ |
| Prontosan | 1.66E+09 | 6.10E+08 |

Figure 3:
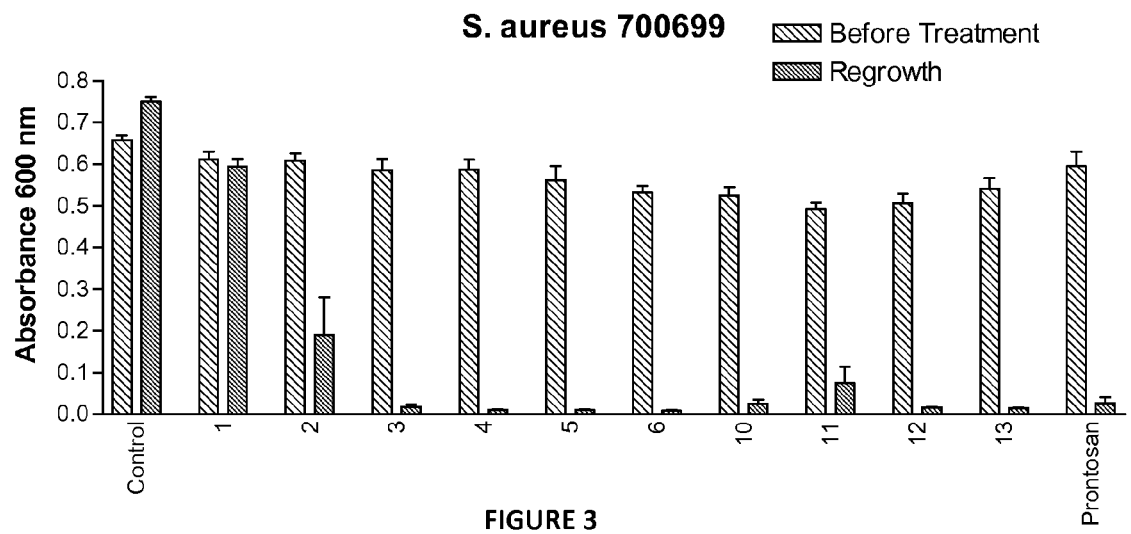
FIG. 3 is a graph showing *Staphylococcus aureus* biofilm regrown for saline, PRONTONSAN® and solutions 1-6 and 10-13.

FIG. 3 is a log kill graph of CFU's before treatment and after 24 hours of regrowth for solutions 1-6 and 10-13 in comparison to saline and Prontosan® relative to a biofilm of *Staphylococcus aureus*, ATCC strain 700699, based upon the absorbance of total bacteria before treatment with the antimicrobial compositions, following a 10 minute exposure to the solutions, and then by regrowth after 24 hours. Graphs with no error bars signify no regrowth.

FIG. 3 shows that the saline negative control had regrowth, as did solutions 1, 2, 3, 10, and 11, as well as the positive control Prontosan®. None of the five test antimicrobial compositions with regrowth (solutions 1, 2, 3, 10 and 11) had the combination of Sensiva® SC 50 and Sensiva® SC 10 with PHMB. In contrast, solutions 4, 5, 6, 12 and 13, which included a polymeric biguanide (PHMB) and vicinal diols (Sensiva® SC 50 and Sensiva® SC 10) exhibited no regrowth of *Staphylococcus aureus* biofilms. These biocidal effects against biofilms are consistent with those observed for *Pseudomonas aeruginosa* biofilms in FIG. 1.

Figure 4:
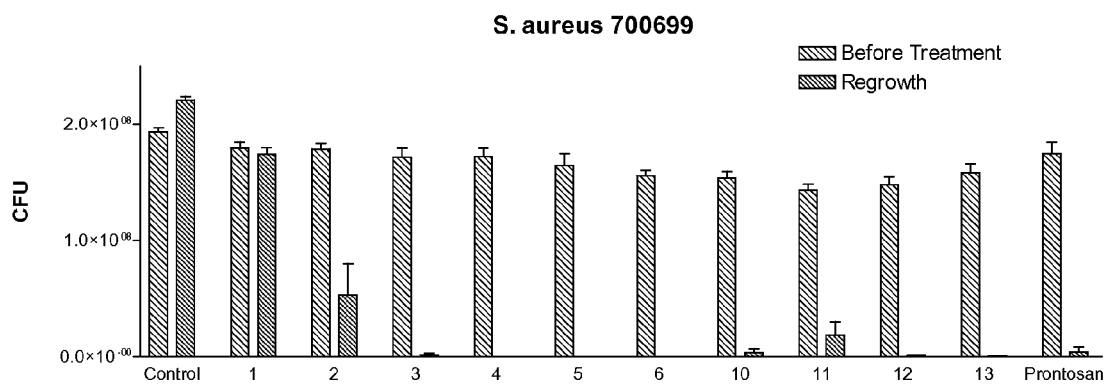
FIG. 4 is a graph showing *Staphylococcus aureus* biofilm log kill graph for saline, PRONTONSAN®, and solutions 1-6 and 11-13.

FIG. 4 is a *Staphylococcus aureus* log kill graph of CFU's before treatment with the antimicrobial compositions, followed by a 10 minute exposure to the solutions, and then by regrowth analysis after 24 hours with the same solutions used to generate FIGS. 1-3. That is, solutions 1-6 and 10-13, wherein the Optical Density data of FIG. 3 was converted to colony forming units of *Staphylococcus aureus* biofilm calculated as a conversion of the Absorbance at 600 nm (A600) to CFU based on a standard curve established for *Staphylococcus aureus*, ATCC 700699. The limit of detection of the spectrophotometer used was 0.001, which means the equivalent of $10^4$ cfu/ml was the lower limit that can be measured. The debris from FIG. 3 was considered baseline. Thus, while the data in FIG. 4 can be interpreted as a kill of at least 8 logs of *Staphylococcus aureus*, the lower limit of quantitation indicates that the effective kill of the bacteria was at least 4 logs for the most efficacious solutions, i.e., solutions 4, 5, 6, 12 and 13, with solutions 4, 5 and 6 being the most effective antimicrobial compositions against *Pseudomonas aeruginosa* biofilm. In contrast, Prontosan® had an effective kill of approximately 1.7 log orders, with regrowth evident in FIGS. 3 and 4. Thus, similar to the antimicrobial results obtained with *Pseudomonas aeruginosa* in FIG. 2, the data of FIG. 4 and Table 3 further support the synergistic interaction of the polymeric biguanide with monoalkyl vicinal diols (e.g., hydrophobic monoalkyl glycol and a hydrophobic monoalkyl glycerol) in reducing or eliminating a *Staphylococcus aureus* biofilm.

TABLE 3

*Staphylococcus aureus* Biofilm Log Kill Tabulated Data for Solutions 1-6 and 11-13, with Saline and Prontosan ®

| Solution | CFU Before Treatment | CFU After 24 h Regrowth |
|---|---|---|
| Control | 1.93E+08 | 2.21E+08 |
| 1 | 1.80E+08 | 1.74E+08 |
| 2 | 1.79E+08 | 5.31E+07 |
| 3 | 1.72E+08 | BLOQ |
| 4 | 1.64E+08 | BLOQ |
| 5 | 1.56E+08 | BLOQ |
| 6 | 1.54E+08 | BLOQ |
| 10 | 1.44E+08 | 3.51E+06 |
| 11 | 1.48E+08 | 1.85E+07 |
| 12 | 1.48E+08 | BLOQ |
| 13 | 1.58E+08 | BLOQ |
| Prontosan | 1.75E+08 | 4.07E+06 |

Figure 5:
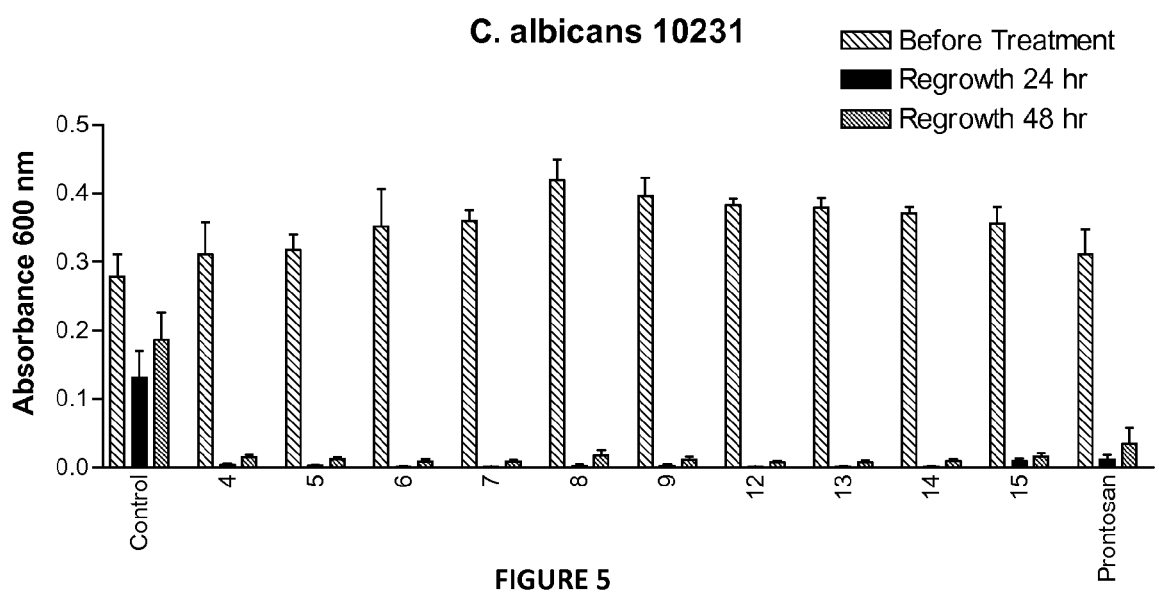
FIG. 5 is a graph showing *Candida albicans* biofilm regrown for saline, PRONTONSAN® and solutions 4-9 and 12-15.

In FIG. 5, solutions 4-9 and 12-15, all with PHMB and Sensiva® SC 50 and Sensiva® SC 10, were studied in comparison to saline and Prontosan® for the regrowth of a biofilm of *Candida albicans* before treatment with the antimicrobial compositions, followed by a 10 minute exposure to the solutions, and then by regrowth analysis after 24 hours and 48 hours. This regrowth study was conducted up to 48 hours because of the slower growth of the *Candida albicans* biofilm in comparison to that of the two bacteria studied. Although all of the test solutions (4-15) solutions contained PHMB and Sensiva® SC 50 and Sensiva® SC 10, some of these solutions contained alexidine or chlorhexidine, with or without sandalwood oil. Neither saline negative control nor Prontosan® positive control contained Sensiva® SC 50 and Sensiva® SC 10.

The study shows that saline solution had the most regrowth, followed by Prontosan® and solutions 8, 9, and 15. The other solutions, 4-7 and 12-14, had little to no regrowth at 24 hours and some regrowth at 48 hours. Solutions 8, 9, and 15 each contained 200 ppm chlorhexidine, in addition to PHMB, indicating that the combination of PHMB and chlorhexidine was not as effective as that of PHMB and alexidine (solutions 6, 7 and 14). Solutions 6, 7, 12, and 13 appeared the most effective against the *Candida albicans* biofilm. Solution 12, which contained 1,500 ppm PHMB, appeared slightly more effective than the other solutions.

Thus, the combination of the polymeric biguanide PHMB with the antimicrobial vicinal diols of a monoalkyl glycol and a monoalkyl glycerol (Sensiva® SC 50 and Sensiva® SC 10), in contrast to the poorer regrowth behavior of Prontosan® solution with PHMB, demonstrated synergistic biocidal ability against the biofilm of *Candida albicans*.

In Table 4, solutions containing glycerol monolaurate (GML, Lauricidin®, monolaurin), an antimicrobial vicinal diol of a monoacyl glycerol, were prepared with PHMB and with Sensiva® SC 50, and with and without Sensiva® SC 10. Solutions containing 0.2 wt % glycerol monolaurate formed needle-like crystals when standing at room temperature, whereas those with 0.1 weight % glycerol monolaurate remained homogeneous at room temperature. The solubility of glycerol monolaurate was enhanced by the combination of surfactant, Sensiva® SC 50 and Sensiva® SC 10.

Using glycerol monolaurate in combination with PHMB and Sensiva® SC 50, with and without Sensiva® SC 10, a minimum inhibitory concentration (MIC) study was conducted using a biofilm of *Pseudomonas aeruginosa*, ATCC 15442, in comparison to Prontosan® for solutions 16-21. These solutions were also varied as to whether they contained alexidine and the surfactant Poloxamer 407 or Tween 80 (TW 80). The MIC study was conducted for three trials per solution and represents the lowest concentration of solution where no bacterial growth is demonstrated. Solutions 18 and 20 had the lowest MIC values of dilution 1:32 of the initial concentration in Table 4, while solutions 16 and 21 had a MIC dilution of 1:16, and solution 19 was equivalent to Prontosan® at an MIC of 1:8. Solution 17 was the least effective, with an MIC dilution of 1:2, indicating that the absence of antimicrobial Sensiva® SC 10, containing 1,2-dihydroxyoctane, a hydrophobic monoalkyl glycol, and the use of Tween 80 as a surfactant, negatively impacted this MIC. These results showed that an antimicrobial composition containing PHMB with the antimicrobial vicinal diols, in particular a hydrophobic monoacyl glycerol (glycerol monolaurate), a hydrophobic monoalkyl vicinal diol (1,2-dihydroxyoctane), and a hydrophobic monoalkyl glycerol (glycerol 1-(2-ethylhexyl)ether, 2-ethylhexylglycerin) is highly effective in the reduction and elimination of *Pseudomonas aeruginosa* biofilm.

TABLE 4

MIC of *Pseudomonas aeruginosa* with Glycerol Monolaurate (Lauricidin ®)

| Composition | Concentration | 16 | 17 | 18 | 19 | 20 | 21 |
|---|---|---|---|---|---|---|---|
| PHMB | ppm | 1000 | 1000 | 1000 | 1000 | 1000 | 1000 |
| ALEX | ppm | 10 | 10 | 10 | 10 | 0 | 0 |
| EDTA | wt % | 0.1 | 0.1 | 0.1 | 0.1 | 0.1 | 0.1 |
| P-407 | wt % | 1 | 0 | 1 | 0 | 1 | 0 |
| TW 80 | wt % | 0 | 1 | 0 | 1 | 0 | 1 |
| HPMC | wt % | 0.2 | 0.2 | 0.2 | 0.2 | 0.2 | 0.2 |
| SC 50 | wt % | 0.3 | 0.3 | 0.3 | 0.3 | 0.3 | 0.3 |
| SC 10 | wt % | 0 | 0 | 0.1 | 0.1 | 0.1 | 0.1 |
| GML | wt % | 0.1 | 0.1 | 0.1 | 0.1 | 0.1 | 0.1 |
| pH | | 5.5 | 5.5 | 5.5 | 5.5 | 5.5 | 5.5 |
| MIC | dilution | 1:16 | 1:02 | 1:32 | 1:08 | 1:32 | 1:16 |

Antimicrobial Dressings

Tests of adsorption of dried solution 4 were also conducted on wound dressing materials, including (a) CVS Dressings Sponges, a rayon/polyester blend used for heavy draining wounds, (b) CVS Gauze Sponges, 100% cotton used for wound dressings and wound packing, (c) CVS Surgical Dressing, a rayon/polyester blend for absorbing fluids, and (d) CVS Eye Pad, a rayon/polyester blend for covering and protecting the eyes. Table 5 provides the results of the amount of dried ingredients from solution 4 that were incorporated into wound dressing materials a-d.

TABLE 5

Weight Percent of Dried, Absorbed Solution 4

| Dressing Material | Wt % Dried Increase |
|---|---|
| (a) Dressing Sponge | 50 |
| (b) Gauze Sponge | 47.2 |
| (c) Surgical Dressing | 23.7 |
| (d) Eye Pad | 30.5 |

Test samples were cut in weights of approximately 0.5 grams. The dressing materials were placed on a glass slide and 3 ml of solution was pipetted onto them. The dressing materials were removed from the slide, which contained excess solution that was not absorbed. The test samples were dried at room temperature for 48 hours in a hood and then weighed. Each of the samples exhibited initial stiffness, but became flexible with manipulation. All dried samples had increased smoothness compared to the original dressing.

For the four substrate materials tested, the amount of solution 4 absorbed, minus water, ranged from 23.7 wt % for the Surgical Dressing to 50.0 wt % for the Dressing Sponge. For the dried Dressing Sponge, the PHMB concentration is calculated to be 2.94 wt % of the dried solution 4 formulation, which includes sodium chloride. Therefore, the concentration of PHMB absorbed into the Dressing Sponge is 1.43 wt %, the concentration of Sensiva® SC 50 is 4.29 wt %, and the concentration of Sensiva® SC 10 is 1.43 wt %. The remaining ingredients maintained the same ratio to PHMB for solution 4 as in Table 1.

By drying the antimicrobial compositions on dressing materials, such materials can be used for controlled delivery of the initial antimicrobial composition to a wound surface because of hydration of the dressing material over time by the wound.

Viscous and Gelled Solutions

In order to increase the concentration of all ingredients for solution 4, viscous solutions and a gel were prepared in concentrations 2, 5 and 10 times (2×, 5× and 10×) the concentration of solution 4. Since the approach used in Table 6 would result in salt concentrations significantly greater than isotonic when said solutions were dried on a dressing, the addition of sodium chloride was eliminated from the 2×, 5×, and 10× solutions derived from solution 4. Solutions 2× and 5× were viscous solutions, with 5× considerably more viscous than 2×, while solution 10× was a firm gel. Concentrated solutions of this type could be applied to dressing materials or coated on a surface, giving higher biocidal activity than the solutions of Table 1.

TABLE 6

Concentrated Solutions of Solution 4

| Concentration | PHMB ppm | EDTA-2 wt % | EDTA-3 wt % | P-407 wt % | HPMC wt % | SC 50 wt % | SC 10 wt % |
|---|---|---|---|---|---|---|---|
| 2X | 2000 | 0.10 | 0.03 | 4 | 0.4 | 0.6 | 0.2 |
| 5X | 5000 | 0.25 | 0.075 | 10 | 1 | 1.5 | 0.5 |
| 10X | 10000 | 0.50 | 0.15 | 20 | 2 | 3.0 | 1.0 |

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

The invention claimed is:

1. An antimicrobial composition, comprising:
at least one polymeric biguanide in an amount of at least 0.05 weight %,
a chelating agent at a concentration of from 0.01 weight % to 1 weight %, and
a vicinal diol component comprising at least one monoalkyl glycol and at least one monoalkyl glycerol, wherein a weight ratio of said at least one polymeric biguanide and said vicinal diol component ranges from 1:0.05 to 1:500, wherein said antimicrobial composition kills at least 99.99% of organisms in a biofilm within ten minutes of treatment with said antimicrobial composition.

2. The antimicrobial composition according to claim 1, wherein
said at least one polymeric biguanide is present in an amount ranging from 0.05 to 1.5 weight % said vicinal diol component,
is present in an amount ranging from 0.05 to 6.0 weight %, based on the total weight of the antimicrobial composition, or both.

3. The antimicrobial composition according to claim 1, wherein said vicinal diol component comprises at least one of (i) a monoalkyl glycol having the following structure:

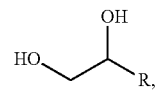

wherein R=$C_3$-$C_{18}$, branched or unbranched alkyl group or alkylene group; and (ii) a monoalkyl glycerol having the following structure:

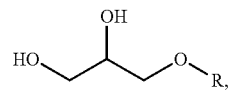

wherein R=$C_3$-$C_{18}$, branched or unbranched alkyl group or alkylene group.

4. The antimicrobial composition according to claim 1, wherein said composition prevents regrowth of biofilm organisms for at least 24 hours after treatment with said antimicrobial composition.

5. The antimicrobial composition according to claim 1, wherein said polymeric biguanide comprises poly(hexamethylene biguanide) and its salts.

6. The antimicrobial composition according to claim 1, further comprising a bis(biguanide) at a concentration of from 10 ppm to 350 ppm.

7. The antimicrobial composition according to claim 6, wherein said bis(biguanide) comprises alexidine and chlorhexidine and salts thereof.

8. The antimicrobial composition according to claim 1, wherein said monoalkyl glycerol is selected from the group consisting of 1-O-heptylglycerol, 1-O-octylglycerol, 1-O-nonylglycerol, 1-O-decylglycerol, 1-O-undecylglycerol, 1-O-dodecylglycerol, 1-O-tridecylglycerol, 1-O-tetradecylglycerol, 1-O-pentadecylglycerol, 1-O-hexadecylglycerol (chimyl alcohol), 1-O-heptadecylglycerol, 1-O-octadecylglycerol (batyl alcohol), 1-O-octadec-9-enyl glycerol (selachyl alcohol), glycerol 1-(2-ethylhexyl)ether (also known as octoxyglycerin, 2-ethylhexyl glycerin, 3-(2-ethylhexyloxy)propane-1,2-diol), glycerol 1-heptyl ether, glycerol 1-octyl ether, glycerol 1-decyl ether, and glycerol 1-dodecyl ether, glycerol 1-tridecyl ether, glycerol 1-tetradecyl ether, glycerol 1-pentadecyl ether, glycerol 1-hexadecyl ether and glycerol 1-octadecyl ether, and combinations thereof.

9. The antimicrobial composition according to claim 1, wherein said monoalkyl glycol is selected from the group consisting of 1,2-propanediol (propylene glycol), 1,2-butanediol, 1,2-pentanediol, 1,2-hexanediol, 1,2-heptanediol, 1,2-octanediol (caprylyl glycol), 1,2-nonanediol, 1,2-decanediol, 1,2-undecanediol, 1,2-dodecanediol, 1,2-tridecanediol, 1,2-tetradecanediol, 1,2-pentadecanediol, 1,2-hexadecanediol, 1,2-heptadecanediol and 1,2-octadecanediol, and combinations thereof.

10. The antimicrobial composition according to claim 1, further comprising at least one monoacyl glycerol, wherein said monoacyl glycerol is selected from the group consisitng of 1-O-decanoylglycerol, monocaprin, 1-O-undecanoylglycerol, 1-O-undecenoylglycerol, 1-O-dodecanoylglycerol, monolaurin, glycerol monolaurate, 1-O-tridecanoylglycerol, 1-O-tetradecanoylglycerol, monomyristin, 1-O-pentadecanoylglycerol, 1-O-hexadecanoylglycerol, 1-O-heptadecanoylglycerol, 1-O-octanyolglycerol, monocaprylin, and combinations thereof.

11. The antimicrobial composition according to claim 1, further comprising a sucrose derivative selected from the group consisitng of surcrose monocaprylate, sucrose monolaurate, sucrose monomyristate and sucrose monopalmitate, and combinations thereof.

12. The antimicrobial composition according to claim 1, further comprising a hydrophobic long-chain or branched monoalkyl alcohol.

13. The antimicrobial composition according to claim 12, wherein the hydrophobic long-chain or branched monoalkyl alcohol is selected from the group consisting of 1-octanol, 1-nonanol, 1-decanol, 1-undecanol, 1-dodecanol, 1-tridecanol, 1-tetradecanol, 1-pentadecanol, 1-hexadecanol, 1-heptadecanol, 1-octadecanol, and 3,7,11,15-tetramethyl-2-hexadecen-1-ol(phytol).

14. The antimicrobial composition according to claim 1 wherein said chelating agent is selected from the group consisting of ethylenediaminetetraacetic acid (EDTA), nitrilotriacetic acid, nitrilotripropionic acid, diethylenetriaminepentaacetic acid, 2-hydroxyethylethylenediaminetriacetic acid, 1,6-diaminohexamethylenetetraacetic acid, 1,2-diaminocyclohexanetetraacetic acid O,O'-bis(2-aminoethyl)ethyleneglycoltetraacetic acid, 1,3-diaminopropanetetraacetic acid, N,N'-bis(2-hydroxybenzyl)ethylenediamine-N,N'-diacetic acid, ethylenediamine-N,N'-diacetic acid, ethylenediamine-N,N'-dipropionic acid, triethylenetetraaminehexaacetic acid, ethylenediamine-N,N'-bis(methylenephosphonic acid), iminodiacetic acid, N,N-bis(2-hydroxyethyl)glycine, 1,3-diamino-2-hydroxypropanetetraacetic acid, 1,2-diaminopropanetetraacetic acid, ethylenediaminetetrakis(methylenephosphonic acid), N-(2-hydroxyethyl)iminodiacetic acid, biphosphonates, editronate, and salts thereof.

15. The antimicrobial composition according to claim 1 further comprising a surfactant at a concentration of from 0.1 weight % to 4 weight %.

16. The antimicrobial composition according to claim 15 wherein the surfactant is selected from the group consisting of poloxamers, poloxamines, Pluronics, diamino block copolymers of ethylene oxide and/or propylene oxide, polyethylene glycol esters of fatty acids, polyoxyethylene or polyoxypropylene ethers of higher alkanes ($C_{12}$-$C_{18}$), polysorbate 20, polysorbate 80, polyoxyethylene lauryl ether, polyoxyethylene stearate, polyoxyethylene propylene glycol stearate, nonylphenol ethoxylates, Tween 80, Miranol, cocoamidopropyl betaine, decyl glucoside, lauryl glucoside and combinations thereof.

17. The antimicrobial composition according to claim 1 comprising a water-soluble polymer at a concentration of from 0.01 weight % to 10 weight %, wherein the water-soluble polymer is selected from the group consisting of methylcellulose, hydroxyethylcellulose, hydroxypropylcellulose, hydroxypropylmethylcellulose, carboxymethylcellulose, polyquaternium-1, polyquaternium-6, polyquaternium-10, guar, hydroxypropylguar, hydroxypropylmethylguar, cationic guar, carboxymethylguar, hydroxypropylchitosan, carboxymethylchitosan, N-[(2-hydroxy-3-trimethylammonium)propyl]chitosan chloride, water-soluble chitosan, hyaluronic acid and its salts, chondroitin sulfate, heparin, dermatan sulfate, amylose, amylopectin, pectin, locust bean gum, alginate, dextran, carrageenan, xanthan gum, gellan gum, scleroglucan, schizophyllan, gum arabic, gum ghatti, gum karaya, gum tragacanth, pectins, starch and its modifications, tamarind gum, poly(vinyl alcohol), poly(ethylene oxide), poly(ethylene glycol), poly(methyl vinyl ether), polyacrylamide, poly(N,N-dimethylacrylamide), poly(N-vinylacetamide), poly(N-vinylformamide), poly(2-hydroxyethyl methacrylate), poly(glyceryl methacrylate), poly(N-vinylpyrrolidone), poly(N-isopropylacrylamide), poly(N-vinylcaprolactam), poly(dimethylaminoethyl methacrylate), poly(dimethylaminopropyl acrylamide), polyvinylamine, and combinations thereof.

18. An antimicrobial composition according to claim 1 comprising 0.05 weight % to 1.0 weight % poly(hexamethylene biguanide) and 0.05 weight % to 4.0 weight % glycerol 1-(2-ethylhexyl)ether and 1,2-dihydroxyoctane.

19. An antimicrobial composition according to claim 1 comprising a pH range of from 4.9 to 7.0.

20. The antimicrobial composition according to claim 1, wherein said antimicrobial solution is part of a wound cleanser.

21. An antimicrobial composition according to claim 20, further comprising 0.1 weight % to 4 weight % surfactant and 0.01 weight % to 10 weight % water-soluble polymer.

22. An article comprising an antimicrobial composition and a material, said antimicrobial composition comprising:
at least one polymeric biguanide in an amount of at least 0.05 weight %,
a chelating agent, and a vicinal diol component comprising at least one monoalkyl glycol and at least one monoalkyl glycerol, wherein a weight ratio of said at least one polymeric biguanide and said vicinal diol component ranges from 1:0.05 to 1:500, wherein a weight ratio of said at least one polymeric biguanide and cheating agent ranges from 2:1 to 1:50, and wherein, when hydrated, said antimicrobial composition kills at least 99.99% of organisms in a biofilm within ten minutes of treatment with said antimicrobial composition, said composition prevents regrowth of biofilm organisms for at least 24 hours after treatment with said antimicrobial composition, or both, wherein said antimicrobial composition is dried on said material.

23. A method of treating a surface, a wound, or a surgical dressing, comprising:
applying an antimicrobial composition to a surface, wherein said antimicrobial composition comprises:
at least one polymeric biguanide in an amount of at least 0.05 weight %,
a chelating agent at a concentration of from 0.01 weight % to 1 weight %, and
a vicinal diol component comprising at least one monoalkyl glycol and at least one monoalkyl glycerol, wherein a weight ratio of said at least one polymeric biguanide and said vicinal diol component ranges from 1:0.05 to 1:500, and wherein said antimicrobial composition kills at least 99.99% of organisms in a biofilm within ten minutes of treatment with said antimicrobial composition, said composition prevents regrowth of biofilm organisms for at least 24 hours after treatment with said antimicrobial composition, or both.

24. The article according to claim 22, wherein the material is selected from the group consisting of a swab, a cloth, a sponge, a foam, a wound dressing material, a non-woven product, a paper product, a polymer film, a catheter, a woven and knitted material.

25. The antimicrobial composition according to claim 1, wherein said antimicrobial composition is present in a form selected from the group consisting of liquids, creams, foams, lotions, gels and aerosols.

26. The antimicrobial composition according to claim 1, wherein:
said at least one polymeric biguanide is present in an amount ranging from 0.05 to 1.5 weight %, said diol component
is present in an amount ranging from 0.05 to 6.0 weight %, used on the total weight of the antimicrobial composition, or both.

27. An antimicrobial composition, comprising:
at least one polymeric biguanide in an amount of at least 0.05 weight %,
a chelating agent at a concentration of from 0.01 weight % to 1 weight %, and
a vicinal diol component comprising at least one monoalkyl glycol and at least one monoalkyl glycerol, wherein a weight ratio of said at least one polymeric biguanide and said vicinal diol component ranges from 1:0.05 to 1:500, wherein-said composition prevents regrowth of biofilm organisms for at least 24 hours after treatment with said antimicrobial composition.

28. The antimicrobial composition according to claim 27, wherein
said at least one polymeric biguanide is present in an amount ranging from 0.05 to 1.5 weight %, said vicinal diol component
is present in an amount ranging from 0.05 to 6.0 weight %, based on the total weight of the antimicrobial composition, or both.

29. The antimicrobial composition according to claim 27, wherein said vicinal diol component comprising at least one of (i) a monoalkyl glycol having the following structure:

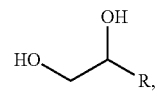

wherein R=$C_3$-$C_{18}$, branched or unbranched alkyl group or alkylene group; and (ii) a monoalkyl glycerol having the following structure:

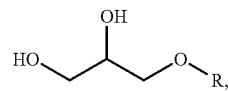

wherein R=$C_3$-$C_{18}$ branched or unbranched alkyl group or alkylene group.

30. The antimicrobial composition according to claim 1, wherein said antimicrobial composition kills at least 99.99% of organisms in a biofilm within ten minutes of treatment with said antimicrobial composition.

31. The antimicrobial composition according to claim 27, wherein said polymeric biguanide comprises poly(hexamethylene biguanide) and its salts.

32. The antimicrobial composition according to claim 27, further comprising a bis(bignanide) at a concentration of from 10 ppm to 350 ppm.

33. The antimicrobial composition according to claim 32, wherein said bis(biguanide) comprises alexidine and chlorhexidine and salts thereof.

34. The antimicrobial composition according to claim 27, wherein said monoalkyl glycerol is selected from the group consisting of 1-O-heptylglycerol, 1-O-octylglycerol, 1-O-nonylglycerol, 1-O-derylglyeerol, 1-O-undecylglycerol, 1-O-dodecylglycerol, 1-O-tridecylglycerol, 1-O-tetradecylglycerol, 1-O-pentadecylglycerol, 1-O-hexadecylglycerol (chimyl alcohol), 1-O-heptadecylglycerol, 1-O-octadecylglycerol (batyl alcohol), 1-O-octadec-9-enyl glycerol (selachyl alcohol), glycerol 1-(2-ethylhexyl) ether (also known as octoxyglycerin, 2-ethylhexyl glycerin, 3-(2-ethylhexyloxy)propane-1,2-diol), glycerol 1-heptyl ether, glycerol 1-octyl ether, glycerol 1-decyl ether, and glycerol 1-dodecyl ether, glycerol 1-tidecyl ether, glycerol 1-tetradecyl ether, glycerol 1-pentadecyl ether, glycerol 1-hexadecyl ether and glycerol 1-octadecyl ether, and combinations thereof.

35. The antimicrobial composition according to claim 27, wherein said monoalkyl glycol is selected from the group consisting of 1,2-propanediol (propylene glycol), 1,2-butanediol, 1,2-pentanediol, 1,2-hexanediol, 1,2-heptanediol, 1,2-octanediol (caprylyl glycol), 1,2-nonanediol, 1,2-decanediol, 1,2-undecanediol, 1,2-dodecanediol, 1,2-tridecanediol, 1,2-tetradecanediol, 1,2-pentadecanediol, 1,2-hexadecanediol, 1,2-heptadecanediol and 1,2-octadecanediol, and combinations thereof.

36. The antimicrobial composition according to claim 27, further comprising at least one monoacyl glycerol, wherein said monoacyl glycerol is selected from the group consisting of 1-O-decanoylglycerol, monocaprin, 1-O-undecanoylglycerol, 1-O-undecenoyiglycerol, 1-O-dodecanoylglycerol, monolaurin, glycerol monolaurate, 1-O-tridecanoylglycerol, 1-O-tetradecanoylglycerol, monomyristin, 1-O-pentadecanoylglycerol, 1-O-hexadecanoylglycerol, 1-O-heptadecanoylglycerol, 1-O-octanoylglycerol, monocaprylin, and combinations thereof.

37. The antimicrobial composition according to claim 27, further comprising a sucrose derivative selected from the group consisting of sucrose monocaprylate, sucrose monolaurate, sucrose monomyristate and sucrose monopalmitate, and combinations thereof.

38. The antimicrobial composition according to claim 27, further comprising a hydrophobic long-chain or branched monoalkyl alcohol.

39. The antimicrobial composition according to claim 38, wherein the hydrophobic long-chain or branched monoalkyl alcohol is selected from the group consisting of 1-octanol, 1-nonanol, 1-decanol, 1-undecanol, 1-dodecanol, 1-tridecanol, 1-tetradecanol, 1-pentadecanol, 1-hexadecanol, 1-heptadecanol, 1-octadecanol, and 3,7,11,15-tetramethyl-2-hexadecen-1-ol (phytol).

40. The antimicrobial composition according to claim 27 wherein said chelating agent is selected from the group consisting of ethylenediaminetetraacetic acid (EDTA), nitrilotriacetic acid, nitrilotripropionic acid, diethylenetriaminepentaacetic acid, 2-hydroxyethylethylenediaminetriacetic acid, 1,6-diaminohexamethylenetetraacetic acid, 1,2-diaminocyclohexanctetraacetic acid, O,O'-bis(2-aminoethyl)ethyleneglycoltetraacetic acid, 1,3-diaminopropanetetraacatic acid, N,N'-bis(2-hydroxybenzyl)ethylenediamine-N,N'-diacetic acid, ethylenediamine-N,N'-diacelic acid, ethylenediamine-N,N'-dipropionic acid, triethylenetetraaminehexaacetic acid, ethylenediamine-N,N'-bis(methylenephosphonic acid), iminodiacetic acid, N,N-bis(2-hydroxyethyl)glycine, 1,3-diamino-2-hydroxypropanetetraacetic acid, 1,2-diaminopropanctetraacetic acid, ethylenediaminetetrakis (methylenephosphonic acid), N-(2-hydroxyethyl) iminodiacetic acid, biphosphonates, editronate, and salts thereof.

41. The antimicrobial composition according to claim 27, further comprising a surfactant at a concentration of from 0.1 weight % to 4 weight %.

42. The antimicrobial composition according to claim 41, wherein the surfactant is selected from the group consisting of poloxamers, poloxamines, Pluronics, diammo block copolymers of ethylene oxide and/or propylene oxide, polyethylene glycol esters of fatty acids, polyoxyethylene or polyoxypropylene ethers of higher alkanes ($C_{12}$-$C_{18}$), polysorbate 20, polysorbate 80, polyoxyethylene lauryl ether, polyoxyethylene stearate, polyoxyethylene propylene glycol stearate, nonylphenol ethoxylates, Tween 80, Miranol, cocoamidopropyl betaine, decyl glucoside, lauryl glucoside and combinations thereof.

43. The antimicrobial composition according to claim 27, comprising a water-soluble polymer at a concentration of from 0.01 weight % to 10 weight %, wherein the water-soluble polymer is selected from the group consisting of methylcellulose, hydroxyethylcellulose, hydroxypropylcellulose, hydroxypropylmethylcellulose, carboxymethylcellulose, polyquaternium-1, polyquaternium-6, polyquaternium-10, guar, hydroxypropyiguar, hydroxypropylmethylguar, cationic guar, carboxymethylguar, hydroxypropylchitosan, carboxymethylchitosan, N-[(2-hydroxy-3-trimethylammonium)propyl]chitosan chloride, water-soluble chitosan, hyaluronic acid and its salts, chondroitin sulfate, heparin, dermatan sulfate, amylose, amylopectin, pectin, locust bean gum, alginate, dextran, carrageenan, xanthan gum, gellan gum, scleroglucan, schizophyllan, gum arabic, gum ghatti, gum karaya, gum tragacanth, pectins, starch and its modifications, tamarind gum, poly(vinyl alcohol), poly(ethylene oxide), poly(ethylene glycol), poly(methyl vinyl ether), polyacrylamide, poly(N,N-dimethylacrylamide), poly(N-vinylacetamide), poly(N-vinylfortnamide), poly(2-hydroxyethyl methacrylate), poly(glyceryl methacrylate), poly(N-vinylpyrrolidone), poly(N-isopropylacrylamide), poly(N-vinylcaprolactam), poly(dimethylaminoethyl methacrylate), poly(dimethylaminopropyl acrylamide), polyvinylamine, and combinations thereof.

44. An antimicrobial composition according to claim 27, comprising 0.05 weight % to 1.0 weight % poly(hexamethylene biguanide) and 0.05 weight % to 4.0 weight % glycerol 1-(2-ethylhexyl) ether and 1,2-dihydroxyoctane.

45. An antimicrobial composition according to claim 27, comprising a pH range of from 4.9 to 7.0.

46. An antimicrobial composition according to claim 27, wherein said antimicrobial solution is part of a wound cleanser.

47. An antimicrobial composition according to claim 46, further comprising 0.1 weight % to 4 weight % surfactant and 0.01 weight % to 10 weight % water-soluble polymer.

48. The antimicrobial composition according to claim 27, wherein said antimicrobial composition is present in a form selected from the group consisting of liquids, creams, foams, lotions, gels and aerosols.

49. The antimicrobial composition according to claim 27, wherein:
said at least one polymeric biguanide is present in an amount ranging from 0.05 to 1.5 weight %, said vicinal diol component
is present in an amount ranging from 0.05 to 6.0 weight %, based on the total weight of the antimicrobial composition, or both.

* * * * *